US005747321A

United States Patent [19]
Yabuta et al.

[11] Patent Number: 5,747,321
[45] Date of Patent: May 5, 1998

[54] **MUTANT *STAPHYLOCOCCUS AUREUS* V8 PROTEASES**

[75] Inventors: Masayuki Yabuta, Tatebayashi; Kazuhiro Ohsuye, Ohta, both of Japan

[73] Assignee: Suntory Limited, Osaka, Japan

[21] Appl. No.: 657,192

[22] Filed: Jun. 3, 1996

[30] Foreign Application Priority Data

Jun. 2, 1995 [JP] Japan .................................. 7-170086

[51] Int. Cl.⁶ .......................... C12N 9/52; C12N 15/00; C12N 1/20; C07H 21/04
[52] U.S. Cl. ................. 435/220; 435/172.1; 435/252.3; 435/320.1; 536/23.2
[58] Field of Search ................. 435/172.1, 220, 435/252.3, 320.1; 536/23.2

[56] References Cited

U.S. PATENT DOCUMENTS

| | | | |
|---|---|---|---|
| 5,532,343 | 7/1996 | Bayne et al. | 530/399 |
| 5,536,655 | 7/1996 | Thomas et al. | 435/209 |

FOREIGN PATENT DOCUMENTS 0 528 686 A2   2/1993   European Pat. Off. .

OTHER PUBLICATIONS

Jean Houmard et al., Staphylococcal Protease: A Proteolytic Enzyme Specific for Glutamoyl Bonds, Dec. 1992, *Proc. Nat. Acad. Sci., USA*, vol. 69, No. 12, pp. 3506–3509.

Cynthia Carmona et al., Nucleotide Sequence for the Serine Protease Gene of *Staphylococcus aureus*, 1987, Strain V8, *Nucleic Acids Research*, vol. 15, No. 16, 6757.

Kazumasa Yoshikawa et al., Recombinant Human Glucagon: Large–Scale Purification and Biochemical Characterization, 1992, *Journal of Protein Chemistry*, vol. 11, No. 5.

Radheshyam K. Jayaswal et al., Cloning and Expression of a *Staphylococcus aureus* Gene Encoding a Peptidoglycan Hydrolase Activity, Oct. 1990, *Journal of Bacteriology*, vol. 172, No. 10, pp. 5783–5788.

M. Yabuta et al., High Expression of a Recombinant Human Calcitonin Precursor Peptide in *Escherichia coli*, 1995, *Appl Microbiol Biotechnol*, 42:703–708.

Jeffrey Vieira et al., The pUC Plasmids, An M13mp7–Derived System For Insertion Mutagenesis And Sequencing With Synthetic Universal Primers, 1982, *Gene* 19:259–268.

Yabuta et al.(1995) J.Fermentation and Bioengineering, 80, 237–243.

*Primary Examiner*—Robert A. Wax
*Assistant Examiner*—Elizabeth Slobodyansky
*Attorney, Agent, or Firm*—Burns, Doane, Swecker & Mathis, L.L.P.

[57] ABSTRACT

Mutant proteases are obtained with one or more mutation sites in the natural V8 protease protein, and with enzyme activities even in the presence of high urea concentrations.

Inactivation of enzyme activity is minimized even in the presence of high concentrations of urea, to thus allow lower amounts of enzyme to be added to urea-containing reaction systems and shorten reaction times. As an additional advantage, the ability to cleave proteins in the presence of high urea concentrations makes it possible to obtain hitherto unobtainable peptide fragments.

24 Claims, 21 Drawing Sheets

PRIMER A ; 5' ACCG<u>CTCGAG</u>GTTATATTACCAAATAACGAT 3'
      XhoI        (SEQ ID No:1)

PRIMER B ; 5' TCGC<u>GTCGAC</u>TTATTGGTCATCGTTGGCAAA 3'
      SalI       (SEQ ID No:2)

Fig.4

```
1                                                  50
MTMITDSLAVVLQRRDWENPGVTQLNRLAAHPPFASWRNSDDARTDRPSQ
                                                   100
QLRSLNGEWRFAWFPAPEAVPDSLLDSDLPEADTVVVPSNWQMHGYDAEL
                                                   150
RLYRRHHRWGRSGSPLRAHEQFLEVILPNNDRHQITDTTNGHYAPVTYIQ
                                                   200
VEAPTGTFIASGVVVGKDTLLTNKHVVDATHGDPHALKAFPSAINQDNYP
                                                   250
NGGFTAENITKYSGEGDLAIVKFSPNEQNKHIGEVVKPATMSNNAETQVN
                                                   300
QNITVTGYPGDKPVATMWESKGKITYLKGEAMQYDLSTTGGNSGSPVFNE
                                                   344
KNEVIGIHWGGVPNEFNGAVFINENVRNFLKQNIEDIHFANDDQ
```

SEQ ID No:3

PRIMER 1 ; 5' GCCGAGGCCTATGACCATGATTACGGAT 3'
(SEQ ID No:4)

PRIMER 8 ; 5' TCGCGTCGACTTATTGGTCATCGTTGGCAAA 3'
SalI
(SEQ ID No:5)

Fig. 8

RESULTS OF IDENTIFYING MUTATION SITES

| PLASMID | BASE CHANGE | AMINO ACID CHANGE |
| --- | --- | --- |
| pV8RPT(-)1 | A440→G | Lys147→Arg |
| pV8RPT(-)5 | A212→G | Asn71→Ser |
| pV8RPT(-)7 | A440→G<br>A212→G | Lys147→Arg<br>Asn71→Ser |
| pV8RPT(-)8 | T132→A | Asp44→Glu |

Fig.13

1                                                                    50
MTMITDSLAVVLQRRDWENPGVTQLNRLAAHPPFASWRNSDDARTDRPSQ
                                                                    100
QLRSLNGEWRFAWFPAPEAVPDSLLDSDLPEADTVVVPSNWQMHGYDAEL
         ↓                                                          150
RLYRRHHRWGRSGSPLRAHEQFLEVILPNNDRHQITDTTNGHYAPVTYIQ
                                                                    200
VEAPTGTFIASGVVVGKDTLLTNKHVVDATHGDPHALKAFPSAINQDNYP
                                                                    250
NGGFTAENITKYSGEGDLAIVKFSPNEQNKHIGEVVKPATMSNNAETQVN
                                                                    300
QNITVTGYPGDKPVATMWESKGKITYLKGEAMQYDLSTTGGNSGSPVFNE
                                  ↓                                 350
KNEVIGIHWGGVPNEFNGAVFINENVRNFLKQNIEDRLYRRHHRWGRSGS
                                                                    400
PLRAHEQFLECGNGKTAFQVLEEYPDSGENIVDALAVFLRRLHSIPVCNC
                                                                    450
PFNSDRVFRLAQAQSRMNNGLVDASDFDDERNGWPVEQVWKEMHKLLPFS
                                                                    500
PDSVVTHGDFSLDNLIFDEGKLIGCIDVGRVGIADRYQDLAILWNCLGEF
                                  532
SPSLQKRLFQKYGIDNPDMNKLQFHLMLDEFF (SEQ ID No:9)

Fig.15

```
1                                                    50
MTMITDSLAVVLQRRDWENPGVTQLNRLAAHPPFASWRNSDDARTDRPSQ
         ↓                                          100
QLRSLNGEWRFAWFPAPEAVPDSLLDSDLPEADTVVVPSNWQMHGYDAEL
                                                    150
RLYRRHHRWGRSGSPLRAHEQFLEVILPNNDRHQITDTTNGHYAPVTYIQ
                                                    200
VEAPTGTFIASGVVVGKDTLLTNKHVVDATHGDPHALKAFPSAINQDNYP
                                                    250
NGGFTAENITKYSGEGDLAIVKFSPNEQNKHIGEVVKPATMSNNAETQVN
                                                    300
QNITVTGYPGDKPVATMWESKGKITYLKGEAMQYDLSTTGGNSGSPVFNE
                                         ↓ 350
KNEVIGIHWGGVPNEFNGAVFINENVRNFLKQNIEDIHFELRLYRRHHRW
                                                    400
GRSGSPLRAHEQFLECGNGKTAFQVLEEYPDSGENIVDALAVFLRRLHSI
                                                    450
PVCNCPFNSDRVFRLAQAQSRMNNGLVDASDFDDERNGWPVEQVWKEMHK
                                                    500
LLPFSPDSVVTHGDFSLDNLIFDEGKLIGCIDVGRVGIADRYQDLAILWN
                            537
CLGEFSPSLQKRLFQKYGIDNPDMNKLQFHLMLDEFF
              (SEQ ID No:15)
```

Fig.16
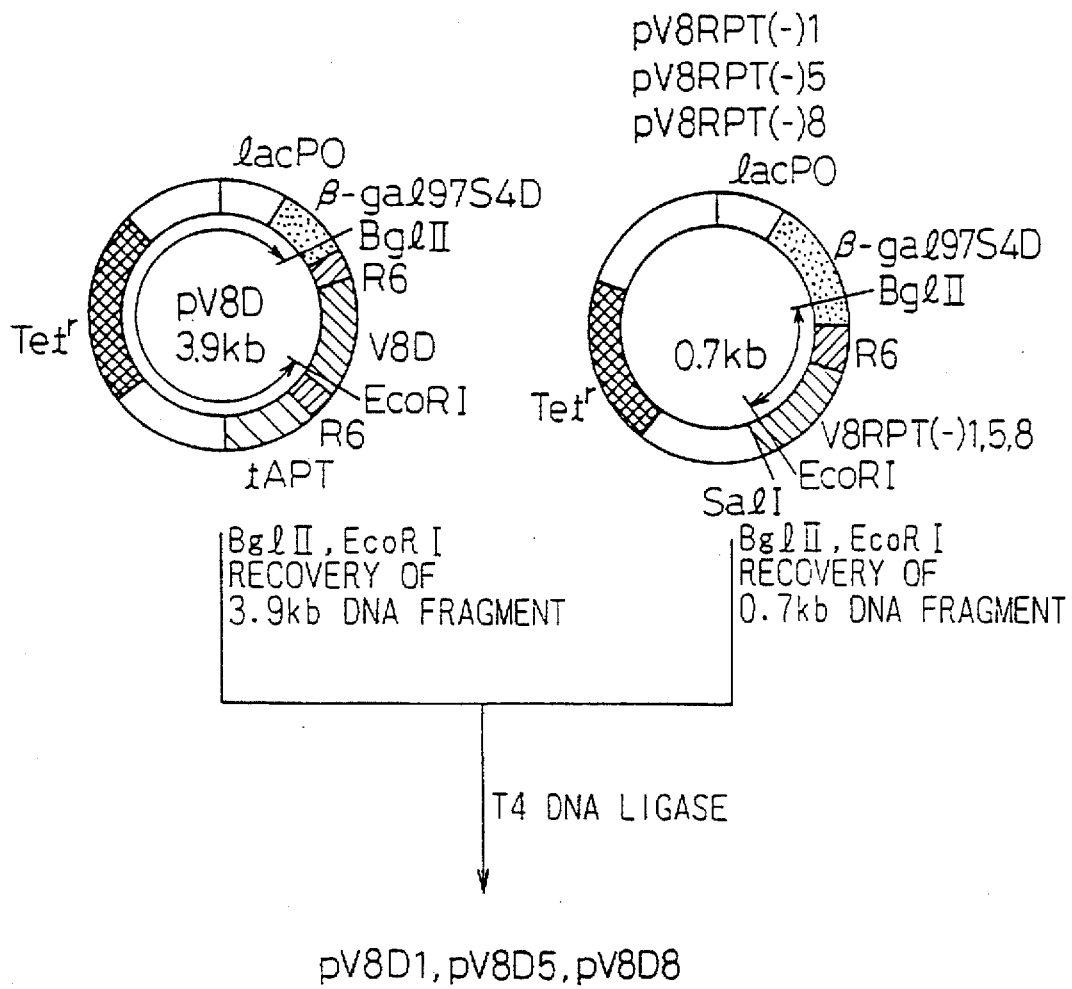
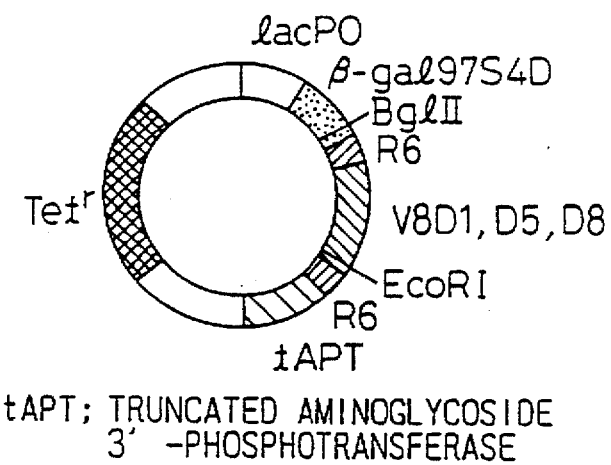
tAPT; TRUNCATED AMINOGLYCOSIDE
3'-PHOSPHOTRANSFERASE Fig. 18
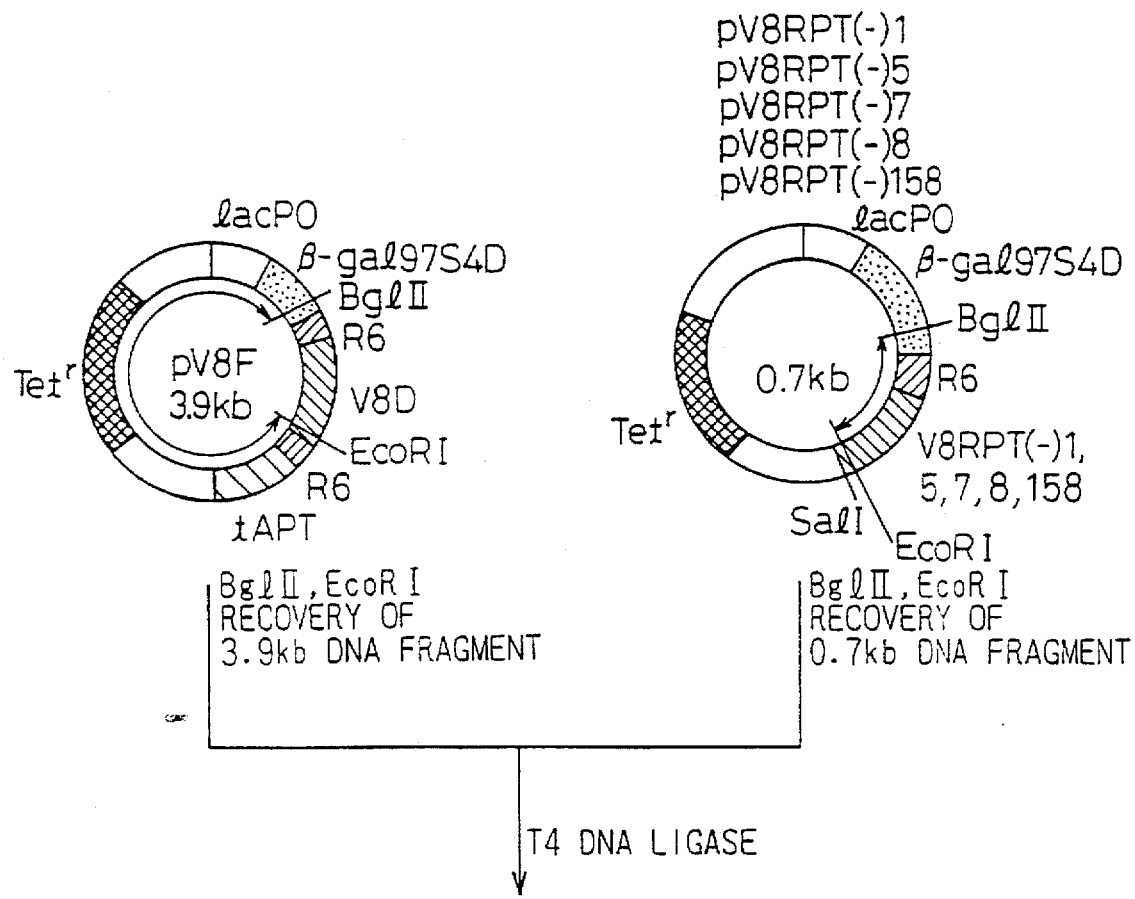
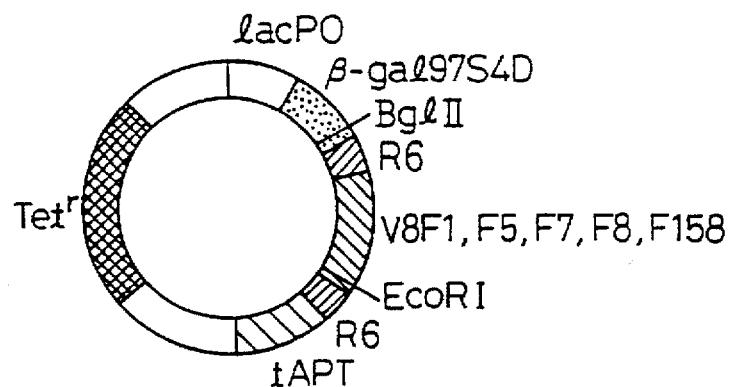

MUTANT *STAPHYLOCOCCUS AUREUS* V8 PROTEASES

BACKGROUND OF INVENTION

1. Field of Invention

The present invention relates to mutants of *Staphylococcus aureus* V8 protease which have enzyme activity even under environmental conditions that promote protein denaturation (hereunder *Staphylococcus aureus* V8 protease will be referred to as "natural V8 protease"), to genes coding for the enzyme proteins, to expression vectors containing the gene, to recombinant cells transformed with the expression vector, and to a method of producing the enzymes.

More specifically, the enzyme proteins of the present invention are mutant V8 proteases with more stable enzyme activity than known natural V8 protease, even under environmental conditions which promote protein denaturation, such as the presence of protein denaturants or high temperature.

2. Related Art

Natural V8 protease is a serine protease secreted by *S. aureus* V8 in culture medium. In 1972, G. R. Drapeau et al. isolated and purified it as a serine protease from *S. aureus* V8 culture medium, which specifically cleaved a C-terminal peptide bond between glutamic acid and aspartic acid (Jean Houmard and Gabriel R. Drapeau (1971), Proc. Natl. Acad. Sci. U.S.A. 69, 3506–3509), and in 1987 Cynthia Carmona et al. reported a DNA nucleotide sequence coding for an amino acid sequence of the natural V8 protease (Cynthia Carmona and Gregory L. Gray (1987), Nucleic Acid Res. 15, 6757).

After the enzyme is expressed as a precursor consisting of 336 amino acid residues, a prepro sequence consisting of 68 amino acid residues is removed and a mature protein is secreted. The enzyme also has a repeating sequence of proline-aspartic acid-asparagine at the C-terminal region (an amino acid sequence of the amino acid Nos. 221 to 256 from the N-terminus), but the present inventors have already discovered that this sequence is not required for enzymatic activity (Japanese Patent Application No. 6-296028).

Although functional analysis of natural V8 protease as an enzyme is still not complete, the enzyme is widely used to determine an amino acid sequences of a protein since it specifically cleaves a C-terminal peptide bond between glutamic acid and aspartic acid. Also, since the natural V8 protease acts on its substrate to some extent even in the presence of urea (about 2M urea), one of the protein denaturation agents which cause protein denaturation, it is used in processes wherein an insoluble fused protein comprising an object peptide expressed in a large amount in a host by recombinant techniques is solubilized with urea, after which the enzyme is allowed to act in the presence of the urea to free the object peptide from the fused protein.

The present inventors have succeeded in producing human calcitonin by gene recombination technique at a high yield using the method described above (Japanese Unexamined Patent Publication No. 5-328992). Also, in cases where human glucagon is expressed as a fused protein in an *E. coli* expression system, natural V8 protease is used to cleave human glucagon from the fused protein (Kazumasa Yoshikawa et al. (1991), Journal of Protein Chemistry 11, 517–525).

Thus, natural V8 protease is used in a wide variety of areas of biochemical research and for the production of peptides by gene recombination. Because natural V8 protease carries out some degree of cleavage reaction even in an enzyme reaction mixture containing urea (about 2M urea) which is known to cause protein denaturation, it is used for the production of useful peptides, etc. by recombination methods.

However, if it were possible to prepare and use a mutant V8 protease with enzyme activity even under environmental conditions which promote greater protein denaturation, in addition to the properties of the natural V8 protease, then the loss of enzyme activity under such environmental conditions could be minimized. The use of a mutant V8 protease with such properties would provide the advantages of (1) requiring less of the enzyme to be added to the reaction system in the presence of the protein denaturant, (2) allowing the reaction time to be shortened, and (3) making possible protein cleavage in the presence of high concentrations of protein denaturants and at high temperatures to provide hitherto unobtainable peptide fragments, for which reasons such a mutant V8 protease has been greatly desired in research and industry.

SUMMARY OF THE INVENTION

It is an object of the present invention to obtain mutant V8 proteases maintaining enzyme activity even under environmental conditions which promote protein denaturation, and the invention further relates to genes coding for the mutant enzyme proteins, to expression vectors containing the gene, to recombinant cells transformed with the expression vector, and to a method of producing the enzyme proteins.

BRIEF DESCRIPTION OF THE DRAWINGS

FIG. 4 shows the amino acid sequence (SEQ ID NO: 3) of the fused protein encoded in plasmid pV8RPT(–). The underlined portion is the sequence portion of the wild V8 protease RPT(–) derivative, and the double underlined portion is the amino acid sequence of the R6 linker.

FIG. 8 lists the results of identification of the mutation sites in the mutant V8 protease RPT (–) derivatives. First nucleotide of wild V8 protease RPT(–) derivative gene is designated as nucleotide No. 1. N-terminus of wild V8 protease derivative RPT(–) is designated as amino acid No. 1.

FIG. 13 shows the amino acid sequence (SEQ ID NO: 9) of the fused protein encoded in plasmid pV8D. The underlined portion is the sequence portion of the wild V8 protease D derivative (V8D), and the double underlined portions are the amino acid sequences of the R6 linkers. The arrows indicate the cleavage sites of OmpT protease.

FIG. 15 shows the amino acid sequence (SEQ ID NO: 15) of the fused protein encoded in plasmid pV8F. The underlined portion is the sequence portion of the wild V8 protease F derivative (V8F), and the double underlined portions are the amino acid sequences of the R6 linkers. The arrows indicate the cleavage sites of OmpT protease.

FIG. 16 shows a process for the construction of plasmids pV8D1, pV8D5 and pV8D8.

FIG. 18 shows a process for the construction of plasmids pV8F1, pV8F5, pV8F7, pV8F8 and pV8F158.

DETAILED DESCRIPTION

Figures 1A, 1B:
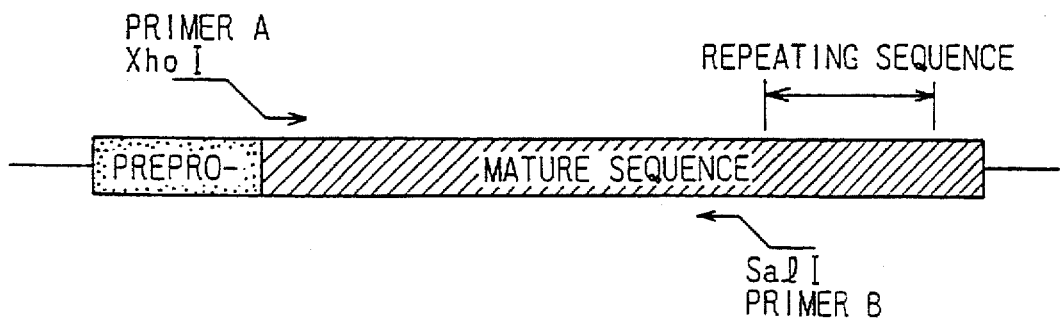
FIG. 1 shows (a) the structure of the *Staphylococcus aureus* V8 protease gene and the annealing sites of the gene, and (b) the base sequences of the PCR primers used for cloning.

The present inventors have completed the present invention upon confirming that the above-mentioned object is sufficiently achieved by using the PCR to induce random mutations in a wild V8 protease derivative gene obtained by the PCR from the natural V8 protease gene, selecting a suitable host, obtaining genes which express mutant V8 protease derivatives exhibiting the most stable enzyme activity under environmental conditions which promote protein denaturation, and producing the gene products (proteins) encoded by the genes, which method is very useful from an industrial standpoint.

In the present specification, a "mutant V8 protease" refers to an enzyme protein having an enzyme activity even under environmental conditions which promote denaturation of natural V8 protease, a "wild V8 protease derivative" refers to an enzyme protein prepared by deleting a C-terminal portion from natural V8 protease, and a "mutant V8 protease derivative" refers to an enzyme protein prepared by causing a mutation in a wild V8 protease derivative.

Three different wild V8 protease derivatives with different C-terminal amino acid sequences were prepared, and these are referred to as (1) wild V8 protease derivative RPT (−) (abbreviated as V8RPT(−)), (2) wild V8 protease D derivative (abbreviated as V8D) and (3) wild V8 protease F derivative (abbreviated as V8F). Also, mutant V8 protease derivatives prepared by introducing mutations in the wild V8 protease derivatives are referred to by attaching the number, for example, "1", "5", "7", "8" or "158" to the end of the derivative name depending on the type of mutation (for example, V8RPT(−)1, V8D5, V8F158, etc.), indicating the introduced mutation.

Environmental conditions under which denaturation of natural V8 protease is promoted are known and include cases where the protein structure changes due to protein denaturation agent or temperature, and the explanation in the present specification deals more specifically with the case of protein denaturation agents, with particular examples of enzyme proteins with sufficient resistance against high concentrations of urea as a protein denaturation agent.

As mentioned above, the amino acid sequence and DNA nucleotide sequence of natural V8 protease has already been elucidated, but the three dimensional structure of the protein is not yet fully understood. Thus, it is completely unknown which amino acids may be changed to impart the resistance against high urea concentration.

Here, the present inventors devised a method of effecting random mutations in the gene coding for this enzyme to isolate a mutant gene for an enzyme which exhibits urea resistance, incorporating the mutated gene into an expression plasmid, transforming host cells with the recombinant plasmid and expressing the gene, and then screening for recombinant expressing enzymes which exhibited enzyme activity even in the presence of 5M urea in which natural V8 protease is inactivated, and the inventors conducted the following research for the purpose of the present invention.

First, a plasmid pV8RPT(−) was constructed incorporating the wild V8 protease derivative RPT(−) gene obtained from the natural V8 protease gene by the PCR. The wild V8 protease derivative RPT(−) is a derivative with a deletion of 48 C-terminal amino acids of natural V8 protease, and plasmid pV8RPT(−) is a plasmid expressing a fused protein of this wild V8 protease derivative RPT(−) with an E. coli β-galactosidase derivative (β-gal97S4D).

Next, the wild V8 protease derivative RPT(−) gene on pV8RPT(−) was treated for random mutations by the PCR, to prepare a pool of mutated wild V8 protease derivative RPT(−) genes. The mutated gene pool was substituted for the wild V8 protease derivative RPT(−) gene on pV8RPT(−) and used to transform E. coli JM101, thus obtaining a number of recombinants. The recombinants were cultured, isopropyl-β-D-thiogalactopyranoside (hereunder, IPTG) was added, and the gene for the fused protein was expressed. After adding urea to the culture medium to a final concentration of about 5M, a synthesized substrate for the enzyme, Z-Phe-Leu-Glu-4-nitroanilide was used for the enzyme reaction.

As a result of screening about 700 recombinant strains, 4 recombinant strains U1, U5, U7 and U8 were obtained which had enzyme activity under the reaction conditions described above. Upon comparing the enzyme activities of these mutant strains in the presence of 5M urea with the natural V8 protease, all were found to have much higher urea resistance than the natural V8 protease.

The plasmids were also isolated from these recombinants and the DNA nucleotide sequences of the mutant V8 protease derivative RPT(−) genes were determined, and as a result, substitution mutations were found of arginine for lysine at the amino acid position 147 in strain U1, of serine for asparagine at the amino acid position 71 in strain U5, of serine for asparagine at the amino acid position 71 and arginine for lysine at the amino acid position 147 in strain U7, and of glutamic acid for aspartic acid at the amino acid position 44 in strain U8. In other words, it became clear that 3 different types of amino acid substitutions had been obtained, and the gene derived from strain U7 was a double mutant with a combination of the amino acid substitutions of strains U1 and U5.

The present inventors have demonstrated for the first time that the amino acid mutations at these positions are necessary for the wild V8 protease derivative RPT(−) to exhibit urea resistance. These amino acid positions are assumed to be important positions from the standpoint of maintaining the protein structure of V8 protease. Thus, the introduction of other amino acids at these positions alters the protein structure of the enzyme of the present invention, thus adequately raising the urea resistance.

Since the protein from the U7 strain with double mutations had the highest urea resistance of the obtained mutant V8 protease derivatives RPT(−), the present inventors expected that if the above-mentioned 3 types of mutations were combined and introduced into the wild V8 protease derivative RPT(−) gene, the resistance might be further increased beyond the urea resistance exhibited by each individual mutant V8 protease derivative RPT(−), and therefore a mutant V8 protease RPT(−) derivative gene with a triple mutation was prepared, and its fused protein was expressed and studied for urea resistance. As a result, the mutant V8 protease derivative RPT(−) with a triple mutation clearly exhibited higher urea resistance than any individual mutant V8 protease derivative RPT(−).

The present inventors then investigated production of this mutant V8 protease derivative. Production was attempted by a method in which the mutant V8 protease D or F derivative, each having a different C-terminal amino acid sequence than mutant V8 protease derivative RPT(−), was first expressed as an inactive inclusion body, and then the active mutant V8 protease D or F derivative was obtained. This was because of the low amount of expression with the mutant V8 protease derivative RPT(−), which is disadvantageous from the standpoint of production. The wild V8 protease D and F derivatives used for preparation of the mutant V8 protease D and F derivatives are derivatives lacking, respectively, 56 and 53 amino acids from the C-terminus of natural V8 protease.

The mutant V8 protease derivative gene was incorporated into plasmids pV8D and pV8F used to express the wild V8 protease D derivative and the wild V8 protease F derivative, and upon culturing, an insoluble fused protein consisting of the $E.\ coil$ β-galactosidase derivative, the mutant V8 protease D or F derivative and an aminoglycoside 3'-phosphotransferase derivative (tAPT) was recovered, the fused protein was cleaved with the endogenous $E.\ coli$ ompT protease in the presence of urea, and the mutant V8 protease D or F derivative was cut out from the fused protein. Then, either the mutant V8 protease D or F derivative was purified through a refolding step and purifying chromatography step, showing that production was possible on an industrial scale.

Each purified mutant V8 protease D or F derivative was then used for a comparison test with their wild forms, under environmental conditions which promote the protein denaturation of each type, e.g. in the presence of urea, in the presence of SDS and at high temperature. As a result, the mutants had lower inactivation rates in the presence of urea or SDS compared to the wild forms, clearly demonstrating that resistance was exhibited against these denaturation agents.

Since the mutant V8 protease F derivative with the triple mutation, i.e., V8F158, has more stable enzyme activity than natural V8 protease even in the presence of 5M urea, a peptide cleavage experiment was conducted using a fused protein of this mutant protein. The fused protein used was β-gal97S4DhCNP-22R5-3, having a structure wherein a protective peptide (β-gal97S4D) and human C-type atrial natriuretic peptide (CNP-22) are fused via a linker peptide, and CNP is released by the V8 protease.

As a result of studying the cleavage efficiency of V8F158 and natural V8 protease on the fused protein of human C-type atrial natriuretic peptide in the presence of 5M urea, it was conclusively shown that V8F158 was able to cleave the fused protein with a much higher cleavage efficiency.

From the examples conducted by the present inventors it is apparent that the mutant V8 protease F derivatives (V8F1, V8F5 and V8F8) exhibit greater resistance against denaturants with enzyme reaction in the presence of 5M urea concentration and 0.1% SDS, than the wild V8 protease F derivatives. However, upon comparison of the enzyme reactions at high temperature (50° C.), the mutant V8 protease F8 derivative (V8F8) had lower thermal stability than the wild V8 protease F derivative (V8F).

Different results were obtained for resistance of the enzymes under denaturing conditions, depending on the different protein denaturing conditions of urea and temperature, and the results may be interpreted as further suggestion that the amino acid residues of the mutated sites are important for maintaining the higher structure of the proteins. Thus, since a person skilled in the art can easily infer that the resistance against temperature will increase if the amino acid at the mutation site of the mutant V8 protease F8 derivative (V8F8) is replaced with another amino acid, the usefulness of the present invention is in no way diminished.

The present inventors have proven the usefulness of the mutant V8 protease derivatives by comparing the enzyme activities of mutant V8 protease derivatives, wild V8 protease derivatives and natural V8 protease under environmental conditions which promote protein denaturation. From the results obtained by the present inventors, it is easily possible for a person skilled in the art to infer that introduction of these mutants into natural V8 protease will result in enzyme activity equal to or greater than that of the natural form, even under environmental conditions which promote protein denaturation.

Consequently, the enzyme proteins of the present invention are mutant V8 proteases which exhibit enzyme activity even under environmental conditions which promote protein denaturation, and preferably these proteases are ones characterized by having one or more mutation sites in the natural V8 protease.

More specifically, preferred embodiments include proteases characterized in that the mutation sites are the aspartic acid at position 44, the asparagine at position 77 and/or the lysine at position 147 from the N-terminus of the natural V8 protease, in which case there may be one, two or three mutation sites.

The most preferred embodiments are:
 (1) a case of one mutation site wherein, counting from the N-terminus of the natural V8 protease, the mutation site is a substitution of glutamic acid for aspartic acid at the position 44, a substitution of serine for asparagine at the position 71 or a substitution of arginine for lysine at the position 147;

(2) a case of two mutation sites wherein, counting from the N-terminus of the natural V8 protease, the mutation sites are aspartic acid at the position 44 and asparagine at the position 71 (in which case glutamic acid is preferably substituted for aspartic acid at the position 44 and serine for asparagine at the position 71), aspartic acid at the position 44 and lysine at the position 147 (in which case glutamic acid is preferably substituted for aspartic acid at the position 44 and arginine for lysine at the position 147), or asparagine at the position 71 and lysine at the position 147 (in which case serine is preferably substituted for asparagine at position 71 and arginine for lysine at position 147); and (3) a case of three mutation sites wherein, counting from the N-terminus of the natural V8 protease, the mutation sites are aspartic acid at the position 44, asparagine at the position 71 and lysine at the position 147 (in which case glutamic acid is preferably substituted for aspartic acid at the position 44, serine for asparagine at the position 71 and arginine for lysine at the position 147).

The method of preparing the genes coding for these mutant V8 proteases may be a method of isolating the genes from S. aureus, for example, a method of designing a primer from the reported natural V8 protease gene sequence followed by isolating them from the gene bank of S. aureus, or the PCR method used by the present inventors. Needless to mention, it is also possible to chemically synthesize the genes from the known natural V8 protease gene sequence of S. aureus.

In the present specification, the mutant V8 protease derivative genes were prepared by the PCR method, but the mutant genes may be prepared using any conventionally known mutation method, such as an in vivo method (mutagenic agent treatment, ultraviolet or radiation treatment, etc.) or one of a variety of in vitro mutation methods. Mutant strains may also be selected according to the present invention by the spontaneous mutation selection method.

For enzyme reaction conditions which promote protein denaturation, the enzyme reaction may be conducted in a reaction medium containing urea or SDS, or at high temperature (for example, 45° C. or higher), or with other protein denaturation agents such as guanidine hydrochloride and various surfactants. Enzyme reaction conditions which have a protein denaturing effect include 2 to 5M urea, 0.01 to 6M guanidine hydrochloride, 0.01 to 10% SDS and temperatures of 45° to 65° C.

The following methods may be used to express the genes for the mutant V8 proteases according to the invention which have enzyme activity even under environmental conditions which promote protein denaturation. In Examples in the present specification, E. coli cells were used as the host cells, but the host cells may also be prokaryotic cells such as Staphylococci, Salmonella, Actinomycetes, Bacillus subtilis, etc. or eukaryotic cells such as filamentous bacteria, yeast, insect cells, animal cells or the like. The mutant V8 protease genes may be introduced into these host cells by any commonly used transformation technique.

The expression plasmid used for the transformation is preferably an expression plasmid with a promoter capable of functionally controlling the expression of a gene downstream of the promoter in the host cells, and by which the direct expression method or so-called fusion protein expression method may be carried out. Also, the vector used may be one capable of homologous gene recombination, with the gene of interest incorporated into the chromosome of a suitable host cell to express the relative protein. By another method, a virus or phage incorporating the gene may be used to infect host cells for expression of the gene of interest.

As a method of producing a mutant V8 protease according to the invention with enzyme activity even under environmental conditions which promote protein denaturation, the present inventors have presented in Examples a very highly efficient production method, but any known common gene recombination technique may be used for the production, without limitation to the method described here.

Examples of possible product methods employing the expression method described above include (1) a method for production by direct expression of the mature protein of interest in the host cells followed by separation and purification of the protein in soluble or insoluble form, (2) a method for production by expression of the protein of interest in the host cells as a fused protein in either soluble or insoluble form, cleavage of the fused protein under conditions which allow cleavage by a processing enzyme, followed by separation and purification of the protein of interest, (3) a method for production by extracellular secretion of the protein of interest followed by separation and purification of the protein, and (4) a method for production by separation and purification of the protein of interest in soluble or insoluble form from the periplasm of the host cells. Needless to mention, when the protein of interest is expressed by direct expression or by the fused protein method, the separation and purification are accomplished through a suitable refolding step in cases where an insoluble protein has been obtained.

In Examples in the present specification, hydrophobic chromatography after refolding is employed for purification of the mutant V8 protease derivatives of the invention, but other methods of purification normally used for protein purification, such as gel filtration, ion chromatography, etc. can provide high degrees of purity. Also, since the enzyme protein is activated once the refolding reaction has been completed and decomposes any contaminating proteins, resulting in the mutant V8 protease derivative as the major protein component after completion of the reaction, the purification is, of course, very easily accomplished.

EXAMPLES

The present invention will now be more fully explained by way of the following examples.

Example 1

Isolation of wild V8 protease derivative RPT(−) gene

The wild V8 protease RPT(−) derivative gene was isolated by the PCR method. Two different PCR primers were designed with the sequences (SEQ ID NOs: 1 and 2) shown in FIG. 1(b), and were synthesized with a DNA synthesizer (Model 392, product of Applied Biosystems Co.). Primers A and B correspond to regions of the V8 protease gene shown in FIG. 1(a), and they contain sequences at their 5' ends recognized by the restriction endonucleases XhoI and SalI, respectively.

The PCR was conducted using S. aureus V8 (ATCC27733) chromosomes isolated and prepared according to the method of Jayaswal, R. K. et al. (J. Bacteriol. 172:5783–5788(1990)) and these PCR primers. To 50 μl of a reaction solution containing 1.0 μM of primer, 1 μg of chromosomal DNA, 50 mM KCl, 10 mM Tris-HCl (pH 8.3), 1.5 mM $MgCl_2$, 0.01% gelatin and 200 µM of dNTP (mixture of dATP, dGTP, dCTP and dTTP) there was added 2.5 units of TaqDNA polymerase, and the PCR was conducted with 30 cycles of 94° C. for 1 minute, 72° C. for 2 minutes and 55° C. for 2 minutes. As a result there was obtained the wild V8 protease RPT(−) derivative gene lacking the prepro sequence and 48 C-terminal amino acids.

The gene was then subjected to agarose gel electrophoresis and purified using SUPREP-2 (Takara Shuzo, KK.), and then cleaved with the restriction enzymes XhoI and SalI, to prepare wild V8 protease derivative RPT(−) gene fragment containing the XhoI and SalI cohesive ends.

Example 2

Construction of expression vector pV8RPT(−) and expression of wild V8 protease derivative RPT(−)

Figure 2:
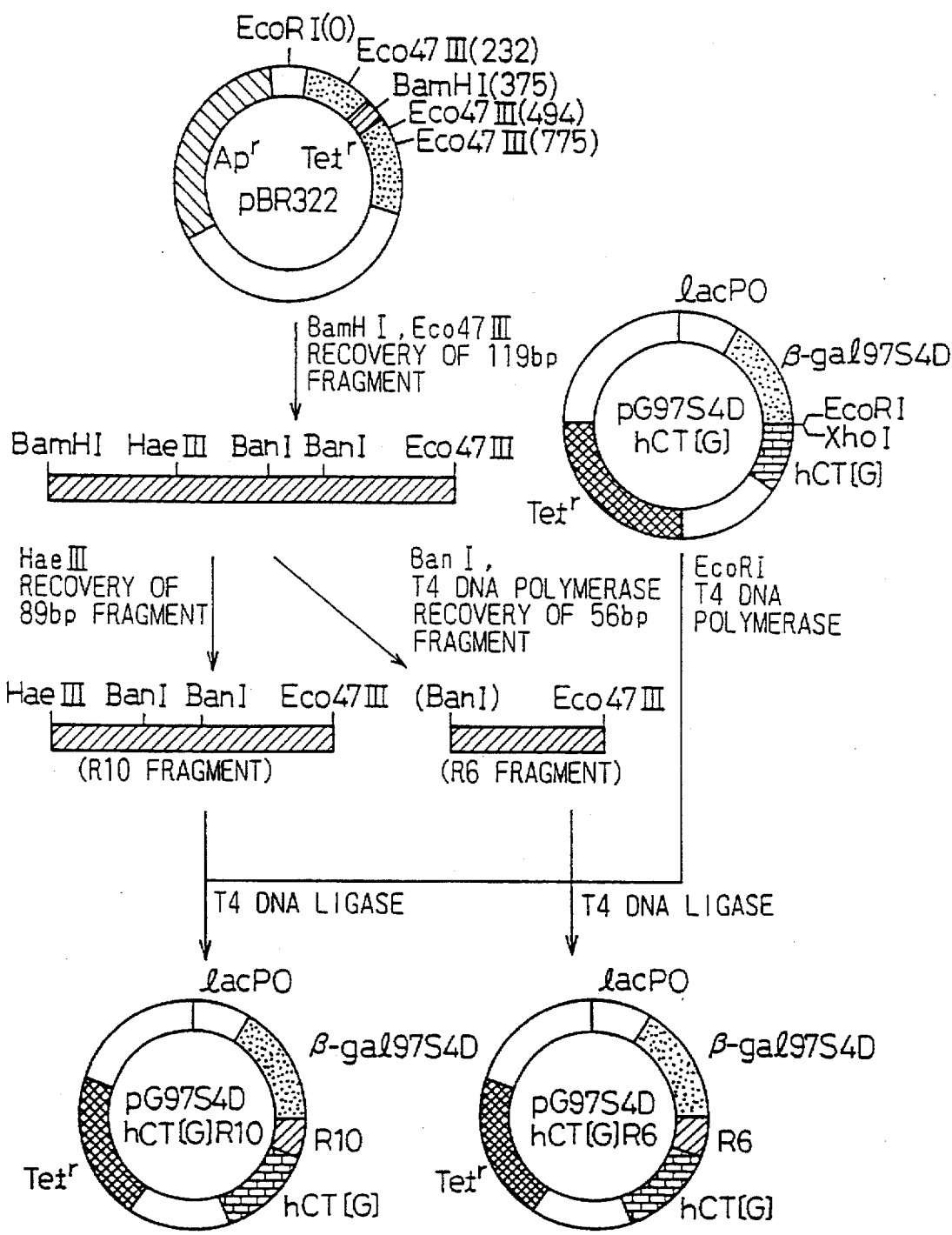
FIG. 2 shows a process for the construction of plasmid pG97S4DhCT[G]R6 and plasmid pG97S4DhCT[G]R10.

The pG97S4DhCT[G]R6 used in this Example (Appl. Microbiol. Biotechnol. (1995) 42, 703–708) is a plasmid with high expression of a fused protein of an *E. coil* β-galactosidase derivative with human calcitonin precursor (hCT[G]), and this plasmid was constructed from plasmid pBR322 and plasmid pG97S4DhCT[G] (FIG. 2).

*E. coli* strain W3110 containing the plasmid pG97S4DhCT[G] has been deposited at the National Institute of Bioscience and Human Technology Agency of Industrial Science and Technology 1-3, Higashi 1-chome Tsukuba-shi Ibaraki-ken 305. Japan, on Aug. 8, 1991 as *Escherichia coli* SBM323, according to the Budapest Treaty, and has been assigned the deposit number FERM BP-3503.

Figure 3:
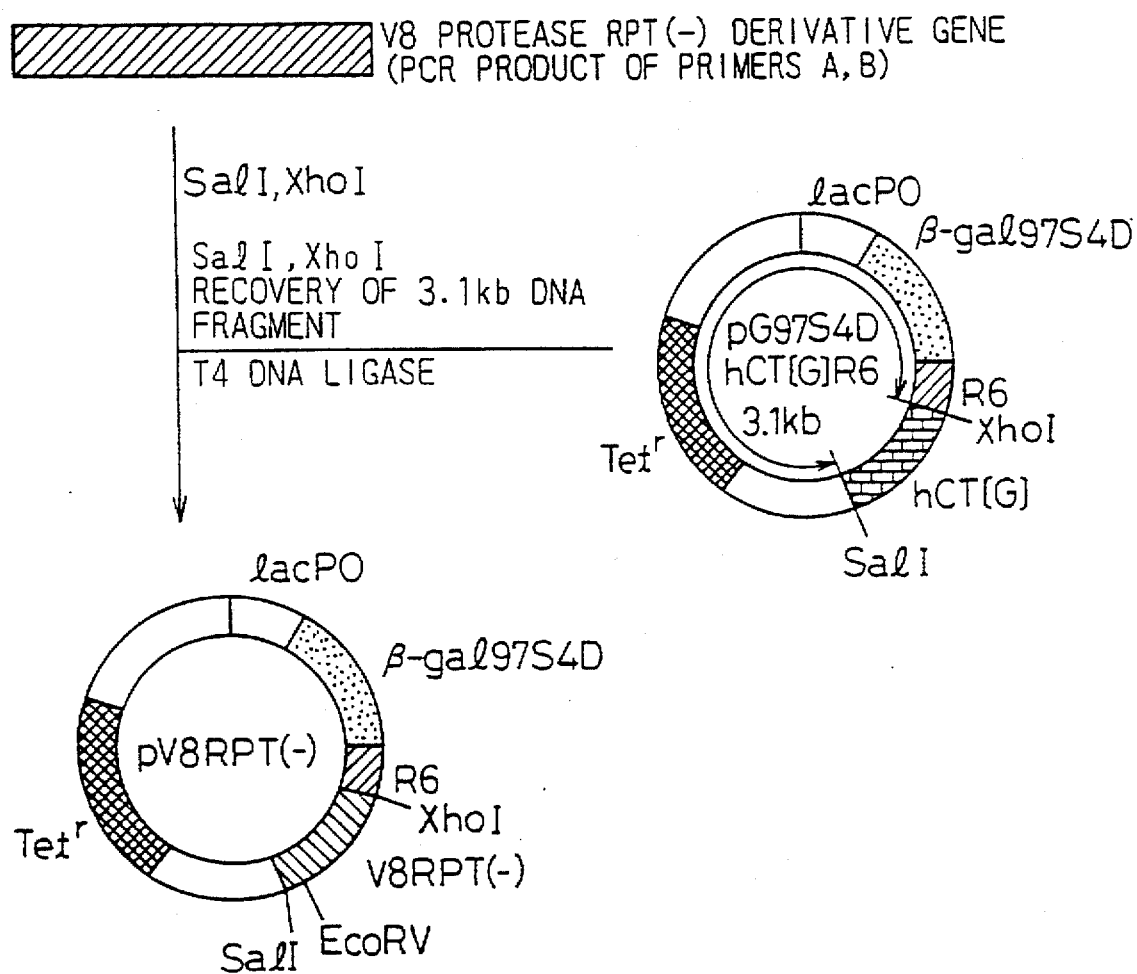
FIG. 3 shows a process for construction of plasmid pV8RPT(–).

In order to express the wild V8 protease derivative RPT(−) gene obtained by the PCR, pG97S4DhCT[G]R6 was treated with XhoI and SalI, and a DNA fragment (3.1 kb) lacking the human calcitonin precursor gene portion was prepared by agarose gel electrophoresis. This DNA fragment was linked with the previously obtained wild V8 protease gene fragment containing the XhoI and SalI cohesive ends using T4 DNA ligase, and JM101 (this strain is available from Takara Shuzo, KK. and elsewhere) was transformed therewith to construct pV8RPT(−) (FIG. 3). FIG. 4 shows the amino acid sequence (SEQ ID NO: 3) for this fused protein (βG97V8RPT(−)) of the wild V8 protease RPT(−) derivative and the β-galactosidase derivative, expressed by the plasmid.

After cultivation of JM101/pV8RPT(−) in 100 ml of LB medium (0.5% yeast extract, 1.0% tryptone, 0.5% NaCl) at 37° C. to an OD660 of 1.0, IPTG was added to a final concentration of 2 mM to induce expression. Cultivation was continued for 2 hours after the addition, and then the cells were collected by centrifugation and suspended in a TE buffer (10 mM Tris-HCl (pH 8.0), 1 mM EDTA) to an OD660 of 5. The suspension was disrupted with an ultrasonic disrupter (Cellruptor: Toso Electric, KK.), and then the insoluble fraction was removed by centrifugation for 5 minutes and the supernatant fraction was used as the crude enzyme solution.

A synthetic substrate (Z-Phe-Leu-Glu-4-nitroanilide; product of Berlinger-Mannheim) was used to measure the activity of the V8 protease. After mixing 20 µl of a 10 mM Z-Phe-Leu-Glu-4-nitroanilide solution (DMSO solution) with 940 µl of a 100 mM Tris-HCl (pH 8.0) buffer solution, 40 µl of the crude enzyme solution was added, and the increase in absorbance at 405 nm upon reaction at room temperature for 5 minutes was measured. A Hitachi spectrophotometer Model U-3200 was used for the measurement.

As a result, an activity corresponding to 8 µg/ml of natural V8 protease was found in the crude enzyme solution prepared from JM101/pV8RPT(−), thus demonstrating that activity is exhibited in the form of a fused protein with the β-galactosidase derivative, and lacking the prepro sequence and the C-terminal repeating sequence.

Example 3

Mutation of V8 protease derivative RPT(−) gene by PCR

The wild V8 protease derivative RPT(−) gene was subjected to mutation by the PCR to obtain V8 proteases with resistance against urea. The pV8RPT(−) obtained in Example 2 (FIG. 3) is a plasmid expressing a fused protein of the wild V8 protease derivative RPT(−) lacking 48 amino acids at the C-terminus (V8RPT(−)) with an *E. coli* β-galactosidase derivative (β-gal97S4D), and the fused protein is expressed in the cellular soluble fraction (this fused protein will hereunder be referred to as βG97V8RPT(−)) has V8 protease activity.

Figures 5A, 5B:
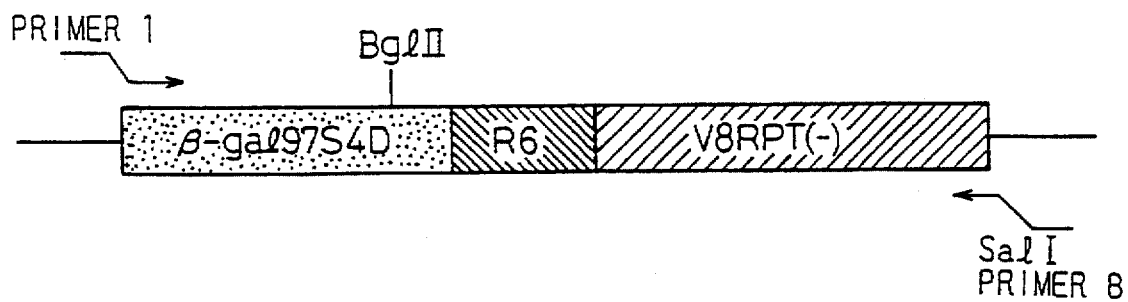
FIG. 5 shows (a) nucleotide sequences (SEQ ID NOs: 4 and 5) of the PCR primers used for cloning and (b) the structure of plasmid pV8RPT(–) and the annealing sites of the genes on the plasmid.

The primers shown in FIG. 5(a) (SEQ ID NOs: 4 and 5) were used for a PCR reaction with the βG97V8RPT(−) gene on the aforementioned plasmid (FIG. 5(b)). To 50 µl of a reaction solution containing 1 µmol of primer, 50 ng of pV8RPT(−), 50 mM KCl, 10 mM Tris-HCl (pH 8.3), 1.5 mM $MgCl_2$, 0.01% gelatin, 10% dimethylsulfoxide (DMSO), 1 mM each of dGTP, dCTP and dTTP and 200 µM of dATP there was added 2.5 units of TaqDNA polymerase, and the PCR was conducted with 30 cycles of 94° C. for 1 minute, 72° C. for 2 minutes and 55° C. for 2 minutes. The resulting PCR product (1 Kbp) was subjected to chloroform treatment and ethanol precipitation and then dissolved in 50 µl of a TE buffer (10 mM Tris-HCl (pH 8.0), 1 mM EDTA).

Example 4

Screening for mutant V8 protease derivatives RPT (−) with urea resistance (primary screening)

Figure 6:
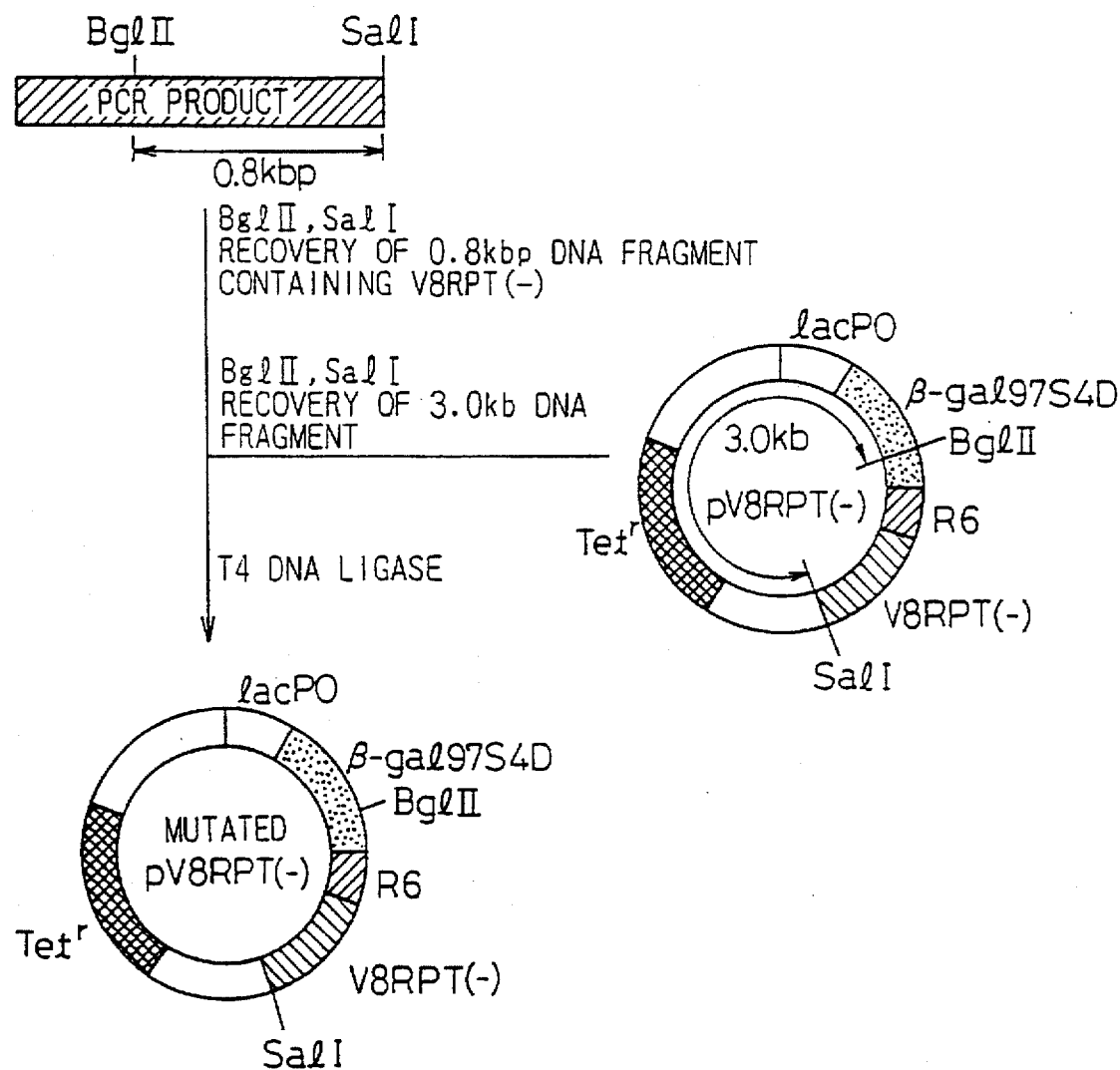
FIG. 6 illustrates the introduction of PCR mutations into plasmid pV8RPT(–).

The PCR product obtained in Example 3 was cleaved with restriction enzymes BglII and SalI, and the 0.8 Kbp fragment containing the mutated wild V8 protease derivative RPT(−) gene was isolated by 0.8% agarose gel electrophoresis, after which a ligation kit (product of Takara Shuzo, KK.) was used to link it with a 3.0 Kbp pV8RPT(−)-derived BglII-SalI fragment (FIG. 6). After completion of the reaction, it was used to transform *E. coli* JM101 (available from In Vitrogen, Catalog No. c660-00) by the calcium chloride method, and transformants were obtained in a 10 µg/ml tetracycline-containing LB agar medium (1% tryptone, 0.5% yeast extract, 0.5% NaCl, 1.5% agar). The restriction enzyme reaction, agarose gel electrophoresis and transformation were all conducted according to conventional methods.

Next, a medium was prepared (pH 7.4) containing 5 mg/ml glycerine, 6 mg/ml $Na_2HPO_4$, 3 mg/ml $KH_2PO_4$, 0.5 mg/ml NaCl, 1.0 mg/ml $NH_4Cl$, 2 mM $MgSO_4.7H_2O$, 0.1 mM $CaCl_2$, 40 µg/ml of each amino acid (20 types), 1 µg/ml thiamine chloride, and 5 µg/ml tetracycline, and 50 µl thereof was dispensed into each well of a 96-well culturing plate (Product No. 25860 of Corning Co.). Each of the transformant strains obtained earlier was seeded in the medium and cultured at 37° C. After one night of static culturing, 50 µl of fresh medium with the same composition was dispensed into each well and static culturing was continued for 3 hours at 37° C. A 10 µl portion of 50 mM IPTG was then added to induce gene expression at 37° C. for one hour.

Next, 30 µl of a 10 mg/ml aqueous lysozyme solution was added, and after standing for 10 minutes, 30 µl of a solution containing 0.1% triton X-100 and 5 mM EDTA (pH 8.0) was added for bacteriolysis.

After subsequently adding 160 µl of 0.1M Tris-HCl (pH 8.0) containing 10M urea (to a final urea concentration of 4.85M) and allowing the mixture to stand at 30° C. for 30 minutes, 10 µl of a DMSO solution containing 20 mM Z-Phe-Leu-Glu-4-nitroanilide (product of Berlinger-Mannheim Co.) was added for reaction overnight at 30° C.

Upon screening about 700 transformants, 4 strains with the strongest degree of yellow coloration produced by decomposition of the enzyme substrate Z-Phe-Leu-Glu-4-nitroanilide were obtained and assigned the names U1, U5, U7 and U8.

Example 5

Screening for mutant V8 protease derivatives RPT (–) with urea resistance (secondary screening)

After culturing the 4 strains (U1, U5, U7 and U8) in 10 ml of LB medium (0.5% yeast extract, 1.0% tryptone, 0.5% NaCl) at 37° C. to an OD660 of 1.0, IPTG was added to a final concentration of 2 mM, and culturing was continued for 2 hours, after which the cells were collected by centrifugal separation.

The cells were then suspended in a TE buffer (10 mM Tris-HCl (pH 8.0), 1 mM EDTA) to an OD660 of 5, and the cells were disrupted with an ultrasonic disrupter (Cellruptor: Toso Electric, KK.). The disrupted solution was centrifuged at 12,000 rpm for 5 minutes to remove the insoluble fraction, and the supernatant fraction was used as the crude enzyme solution.

For measurement of the protease activity, 20 µl of a 20 mM Z-Phe-Leu-Glu-4-nitroanilide solution was mixed with 940 µl of a 50 mM Tris-HCl (pH 8.0) buffer solution, 40 µl of the crude enzyme solution was added, and the increase in absorption at 405 nm upon reaction at room temperature for 5 minutes was measured using a Hitachi spectrophotometer Model U-3200. After measuring the V8 protease activity of the crude enzyme solutions from the 4 strains, an amount of each crude enzyme solution corresponding to 0.2 µg enzyme activity of natural V8 protease (for example, endoproteinase Glu-C, product of Berlinger-Mannheim Co.) was used to determine the change in reactivity over time in the presence of urea. The experiment was conducted with a reaction solution containing 5M urea, 50 mM Tris-HCl (pH 8.0), 0.4 mM Z-Phe-Leu-Glu-4-nitroanilide and 2% DMSO, measuring the change in the reaction with time based on the increase in absorbance at 405 nm (using a Hitachi spectrophotometer Model U-3200). The results are shown in FIG. 7.

Figure 7:
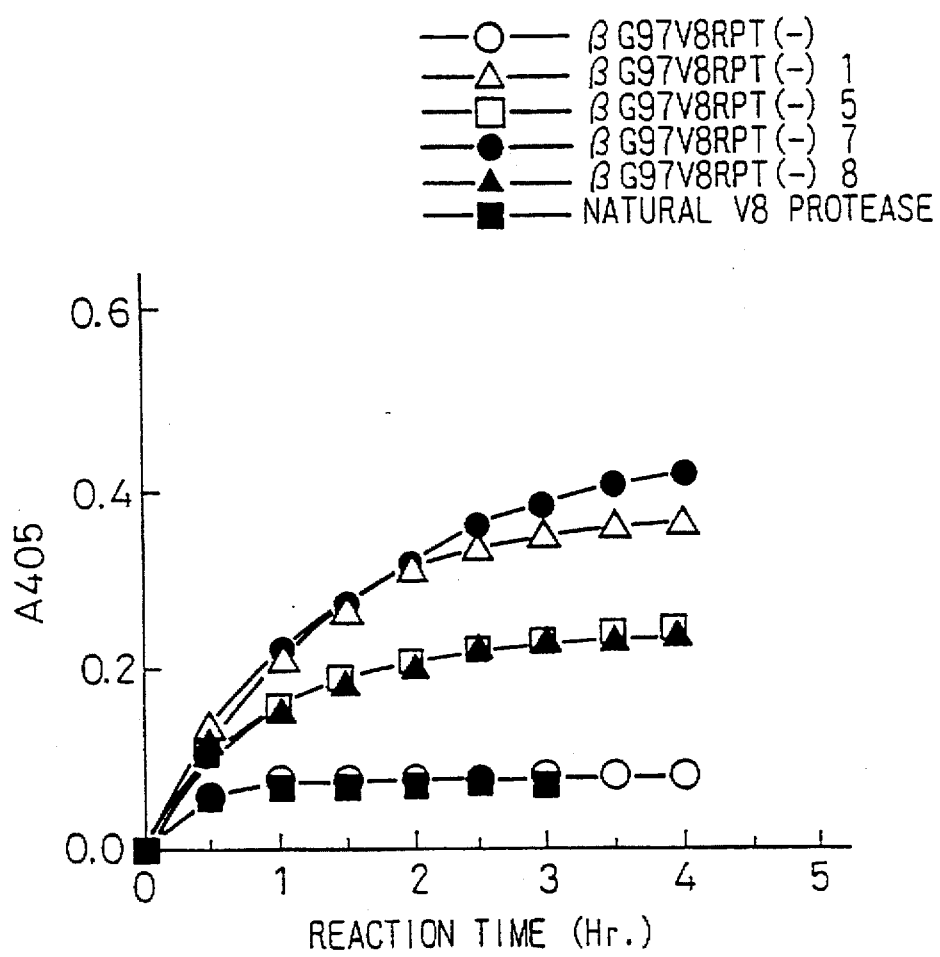
FIG. 7 shows the changes with time elapse in the reactivity of mutant V8 protease RPT (–) derivatives in the presence of 5M urea.

As FIG. 7 clearly shows, the fused proteins of the mutant V8 protease derivatives RPT(–) produced by mutant strains U1, U5, U7 and U8 (hereunder referred to respectively as βG97V8RPT(–)1, βG97V8RPT(–)5, βG97V8RPT(–)7 and βG97V8RPT(–)8) maintained decomposition activity on the substrate, exhibiting resistance against urea, in contrast with the wild form βG97V8RPT(–).

Example 6

Identification of mutation sites and preparation of mutant V8 protease derivative RPT(–) fused protein with combined mutations The plasmids were isolated and purified from the mutant strains U1, U5, U7 and U8 by conventional methods. These plasmids will hereunder be referred to as pV8RPT(–)1, pV8RPT(–)5, pV8RPT(–)7 and pV8RPT(–)8.

The DNA nucleotide sequences of the mutant V8 protease derivative genes on each of the plasmids were then determined using a DNA sequencer (A.L.F. DNA Sequencer), manufactured by Pharmacia. Determination of the DNA nucleotide sequences was accomplished by the fluorescent label method employing fluoro-dUTP, using an AutoRead Sequencing Kit, also manufactured by Pharmacia, and the following primers were used.

Primer A (a sense primer annealing with a portion from nucleotide Nos. 1 to 22, nucleotide No. 1 being the first base of the gene coding for the wild V8 protease RPT(–) derivative shown in FIG. 4);

5'-ACCGCTCGAGGTTATATTACCAAATAACGAT-3' (SEQ ID NO: 6)

Primer D1 (a sense primer annealing with a portion from nucleotide Nos. 266 to 294 of the same);

5'-CAGGCGAAGGAGCGCTAGCAATAGTTAAA-3' (SEQ ID NO: 7)

Primer D2 (an antisense primer annealing with a portion from nucleotide Nos. 266 to 294 of the same);

5'-TTTAACTATTGCTAGCGCTCCTTCGCCTG-3' (SEQ ID NO: 8)

The DNA sequencing procedure described in the manufacturer's laboratory manual was followed. As a result it was demonstrated that the mutations shown in FIG. 8 had occurred in the mutant V8 protease derivatives RPT(–) produced by the 4 mutant strains. In particular, the mutant V8 protease derivative on pV8RPT(–)7 was a double mutation, which was shown to be a combination of the mutations of pV8RPT(–)1 and pV8RPT(–)5. Thus, it was concluded that the double mutation was the reason for the higher activity of βG97V8RPT(–)7 shown in FIG. 7 compared to βG97V8RPT(–)1 and βG97V8RPT(–)5. This shows the possibility of creating a highly urea-resistant enzyme by combining the mutations.

Figure 9:
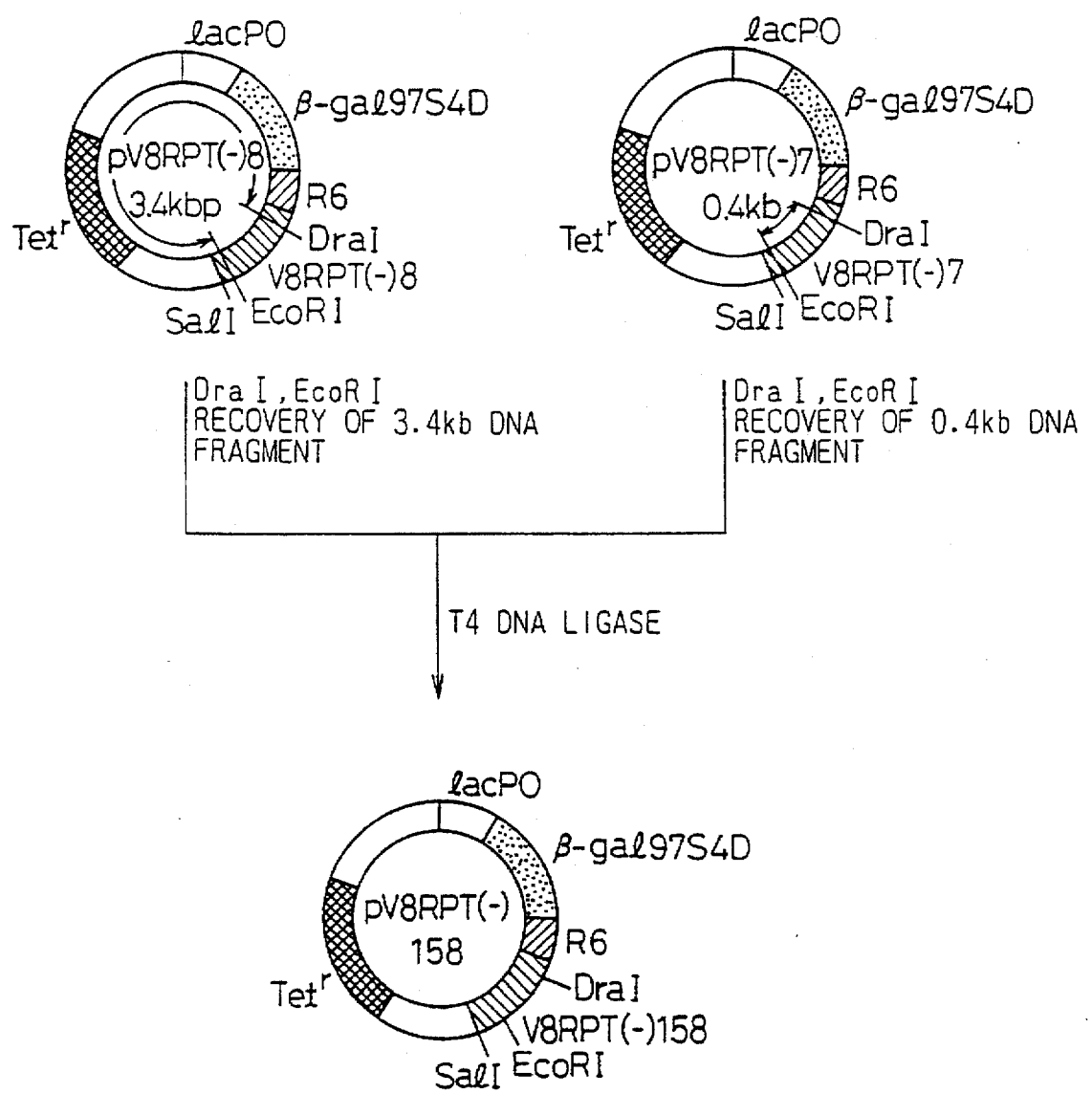
FIG. 9 shows a process for the construction of plasmid pV8RPT(–)158.

In order to confirm this, plasmid pV8RPT(–)158 was constructed, having all 3 of the obtained mutations. Restriction enzyme sites (DraI, EcoRI) present on the V8 protease gene were used for the construction according to the procedure outlined in FIG. 9. The 0.4 Kbp DraI-EcoRI fragment from pV8RPT(–)7 was exchanged for that of pV8RPT(–)8 to construct pV8RPT(–)158.

Figure 10:
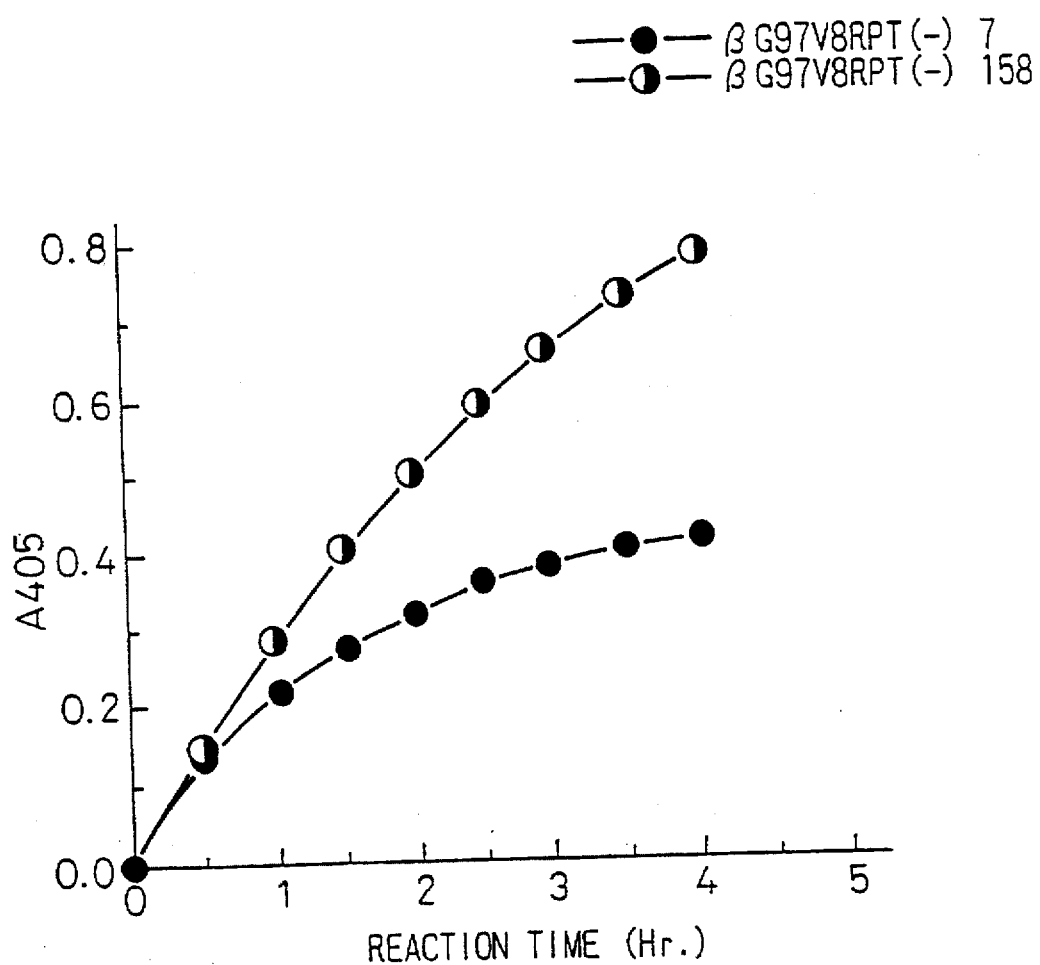
FIG. 10 shows the changes with time elapse in the reactivity of mutant V8 protease RPT(–) derivatives having double and triple mutations, in the presence of 5M urea.

The triple mutant V8 protease derivative RPT(–) derived from this plasmid (βG97V8RPT(–)158) was studied for changes in reactivity with time elapse in the presence of 5M urea, according to the procedure described above (see FIG. 10). As a result, βG97V8RPT(–)158 was demonstrated to have a more prolonged decomposition reaction on the synthetic substrate than βG97V8RPT(–)7, by which it was understood that the 3 mutations impart urea resistance in a cumulative manner.

Example 7

Construction of expression vector pV8D

Figure 11:
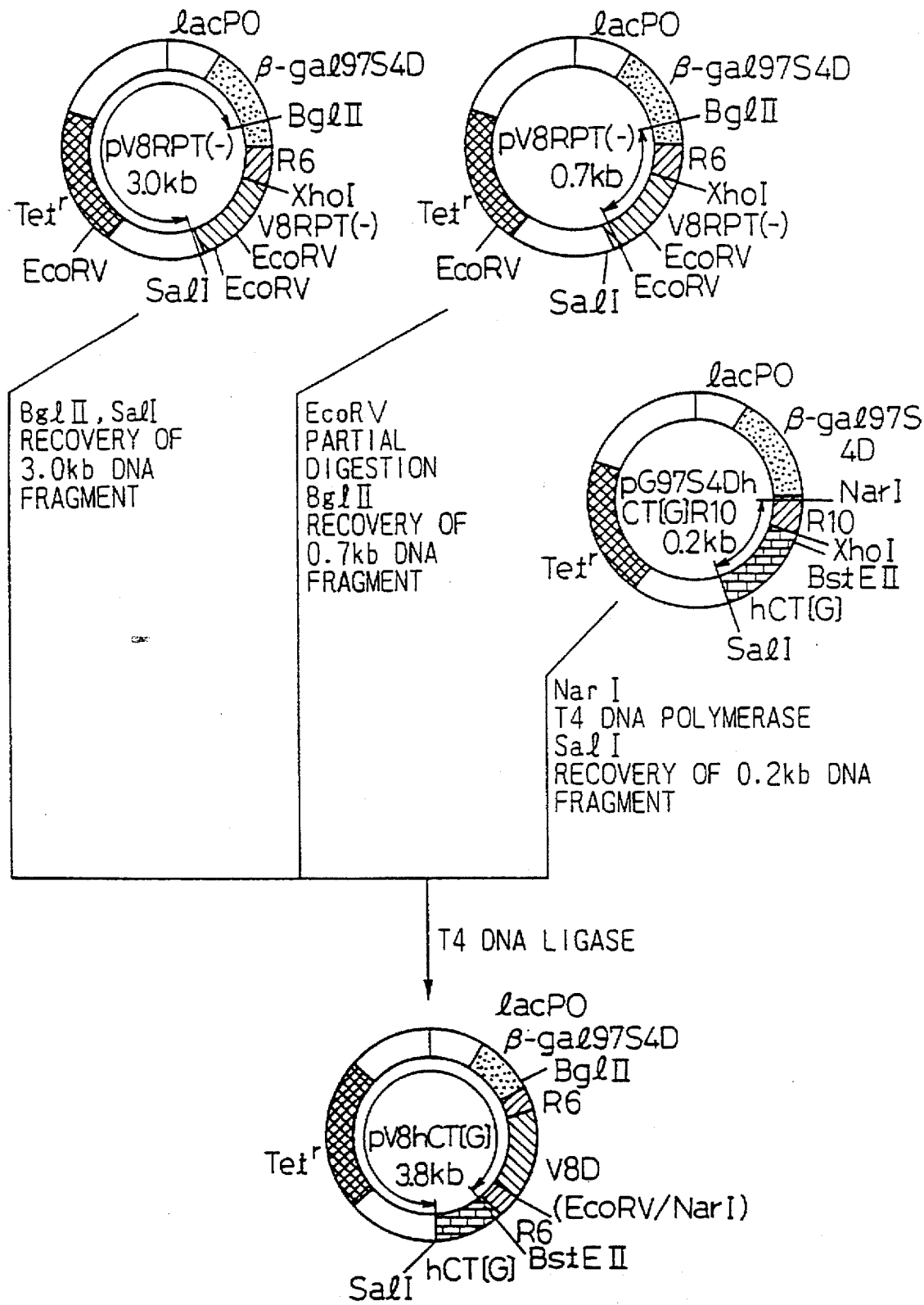
FIG. 11 shows a process for the construction of plasmid pV8hCT[G].
Figure 12:
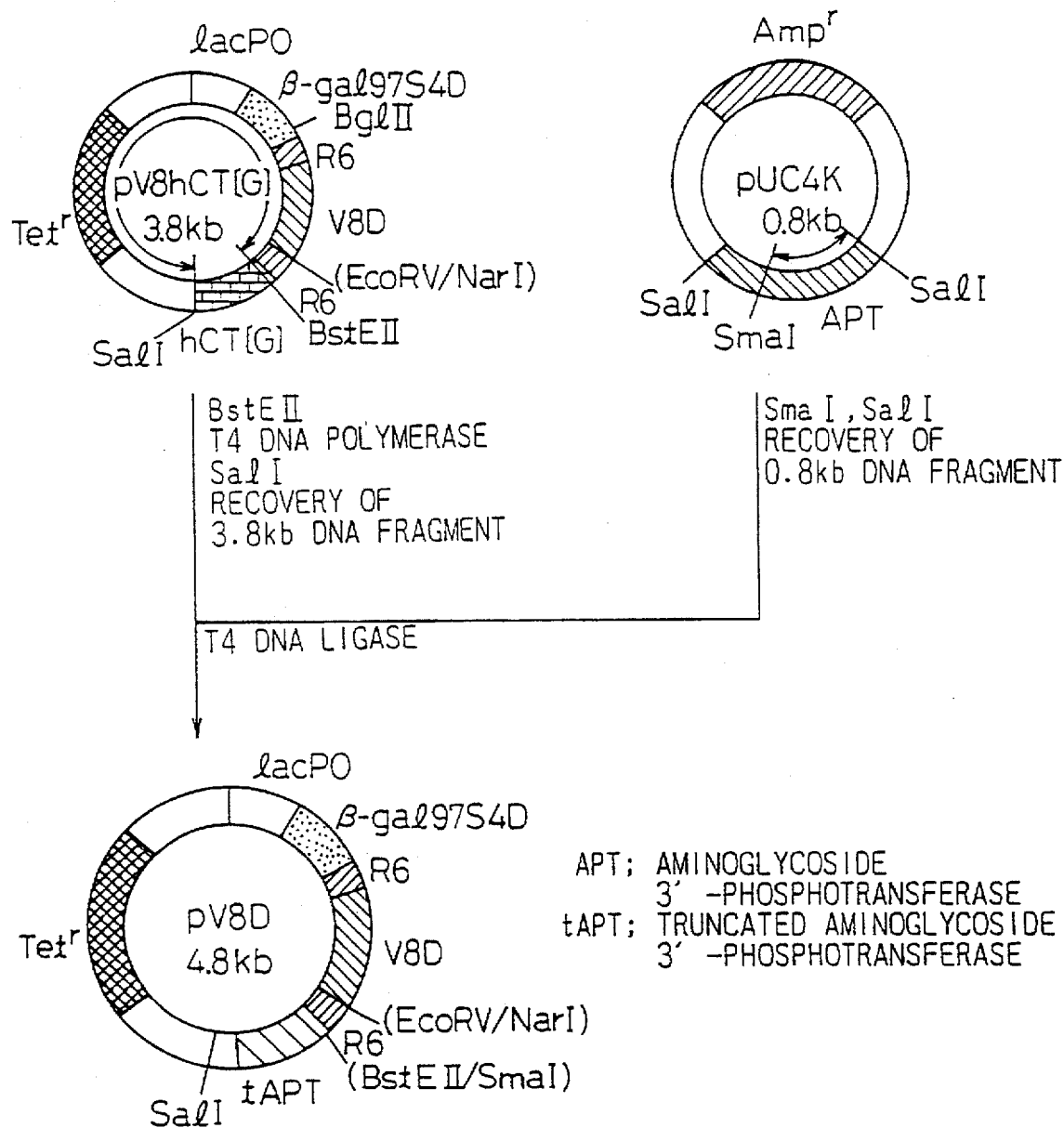
FIG. 12 shows a process for the construction of plasmid pV8D.

Plasmid pV8D expressing the wild V8 protease D derivative (V8D) as an inactive inclusion body was constructed according to the procedure outlined in FIGS. 11 and 12. First, a BglII-SalI fragment (3.0 kb) and EcoRV-BglII fragment (0.7 kb) were prepared from pV8RPT(–), and were linked with a NarI-SalI fragment (0.2 kb) prepared from pG97S4DhCT[G]R10 to obtain pV8hCT[G] (FIG. 11). The plasmid pG97S4DhCT[G]R10 (Appl. Microbiol. Biotechnol. (1995) 42, 703–708) may be constructed from plasmid pBR322 and plasmid pG97S4DhCT[G] in the same manner as pG97S4DhCT[G]R6 in Example 2.

Next, the hCT[G] portion of the obtained pV8hCT[G] (the 0.1 kb BstE-SalI fragment) was replaced with a 0.8 kb SmaI-SalI fragment containing the aminoglucoside 3'-phosphotransferase gene (APT) region of pUC4K (Vieira, J. and Messing, J., Gene 19, 259 (1982); readily available as Product No. 27-4958-01 of Pharmacia Biotech), to construct pV8D (FIG. 12). FIG. 13 shows the amino acid sequence (SEQ ID NO: 9) of the wild V8 protease D derivative (V8D) fused protein expressed by this plasmid. The wild V8 protease D derivative is a derivative lacking 56 of the C-terminal amino acids from the natural protease.

The fused protein was prepared using the portion of natural V8 protease to the 212th amino acid from the N-terminus (the EcoRV site). That is, the fused protein has a structure wherein the β-galactosidase derivative and part of the aminoglucoside 3'-phosphotransferase (tAPT) are fused at the N-terminal and C-terminal portions of the wild V8 protease D derivative (V8D), respectively, via R6 linkers.

The R6 linker has the amino acid sequence:

Arg Leu Tyr Arg Arg His His Arg Trp Gly Arg Ser Gly Ser Pro
Leu Arg Ala His Glu Gln Phe Leu Glu    (SEQ ID NO: 10)

and has a structure wherein the peptide bond between RR in the sequence is cleaved by ompT protease of *E. coli*.

Example 8

Construction of expression vector pV8F

Plasmid pV8F expressing the wild V8 protease F derivative (V8F) as an inactive inclusion body is a plasmid which expresses a fused protein which is a derivative of the aforementioned wild V8 protease D derivative (V8D) having a V8 protease portion 3 amino acids longer at the C-terminal end, and it was constructed in the following manner by the PCR method and gene cloning.

First, primer IV (SEQ ID NO: 11)

5'-ACCGCTCGAGGTTATATTACCAAATAACGAT-3'
       XhoI and primer V (SEQ ID NO: 12)

5'-GACTTATTGGTCATCGAGCTCAAAATGGATATC-3'
                        SacI were synthesized, and 0.1 μg of pV8RPT(−) constructed in Example 2 was used as the template DNA for an amplification reaction at the wild V8 protease derivative gene end, after which it was cleaved with EcoRI and SacI to prepare a 0.1 kb gene fragment.

Meanwhile, primer VI (SEQ ID NO: 13):

5'-AATATTGAAGAGCTCCGCCTATATCGCCGACAT-3'
            SacI and primer VII (SEQ ID NO: 14)

5'-GAATGGCAAAAGCTTATGCATTTCTTT-3'
                   EcoT22I were also synthesized and 0.1 μof pV8D was used as a template DNA for an amplification reaction of the R6 linker sequence and the aminoglucoside 3'-phosphotransferase gene portion, after which it was cleaved with EcoT22I and SacI to prepare a 0.3 kb gene fragment. The PCR was conducted under the same conditions as Example 1.

Figure 14:
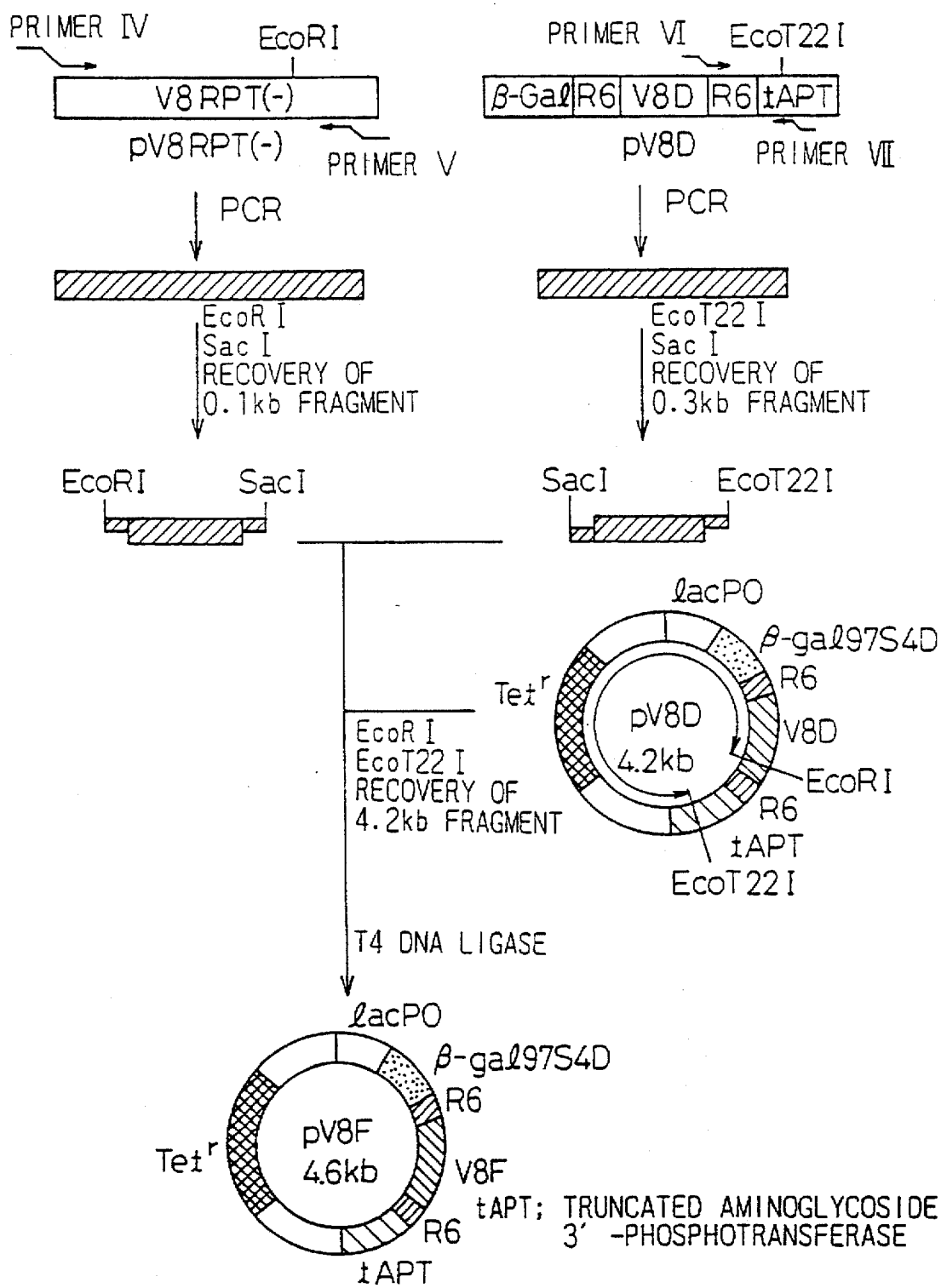
FIG. 14 shows a process for the construction of plasmid pV8F. The V8F gene is the gene coding for the wild V8 protease F derivative (V8F).

The 0.1 kb and 0.3 kb gene fragments obtained as described above were linked with an EcoRI-EcoT22I fragment (4.2 kb) from pV8D to construct pV8F (FIG. 14). FIG. 15 shows an amino acid sequence (SEQ ID NO: 15) of the wild V8 protease F derivative (V8F) fused protein expressed by this plasmid. The wild V8 protease F derivative is a derivative lacking 53 C-terminal amino acids from the natural protease.

Example 9

Production of mutant V8 protease D (V8D) and F derivatives (V8F) and confirmation of urea resistance Plasmids pV8D and pV8F were used to attempt high expression of mutant V8 protease D (V8D) and F (V8F) derivatives.

(1) Mutant V8 protease D derivative

As shown in FIG. 16, the 0.7 kbp BglII-EcoRI fragments derived from pV8RPT(−)1, pV8RPT(−)5 and pV8RPT(−)8 were each inserted into the 3.9 kbp BglII-EcoRI fragment to construct PVD1, pV8D5 and pV8D.

After culturing JM101 having each of the plasmids in a fermenter (30L Kit Fermenter, product of Komatsugawa Chemical Instruments) in a medium (20 L, pH 7.0) containing 4 g/L $K_2HPO_4$, 4 g/L $KH_2PO_4$, 2.7 g/L $Na_2HPO_4$, 0.2 g/L $NH_4Cl$, 1.2 g/L $(NH_4)_2SO_4$, 4 g/L yeast extract, 2 g/L $MgSO_4.7H_2O$, 40 mg/L $CaCl_2.2H_2O$, 40 mg/L $FeSO_4.7H_2O$, 10 mg/L $MnSO_4.nH_2O$, 10 mg/L $AlCl_3.6H_2O$, 4 mg/L $CoCl_2.6H_2O$, 2 mg/L $ZnSo_4.7H_2O$, 2 mg/L $Na_2MoO_4.2H_2O$, 1 mg/L $CuCl_2.2H_2O.5$, mg/L $H_3BO_4$ and 10 mg/L tetracycline, at 37° C. to an OD660 of 10 while successively adding glycerine, IPTG was added to a final concentration of 2 mM and culturing was continued for 3 hours.

The culture medium truth obtained was subjected to homogenization with a MantonGaullin homogenizer (Model 15M-8TBA, from MantonGaullin Co.) under conditions of 600 Kg/cm², and the precipitating fraction was recovered by centrifugation at 7000 rpm for 30 minutes. After adding deionized water until the OD660 of the precipitate reached 100, 15 ml thereof was taken, and 2.5 ml of 1M Tris-HCl (pH 8.0), 250 μl of 1M dithiothreitol (DTT) and 12 g of urea were added to dissolve the inclusion bodies, after which deionized water was added to prepare 50 ml and the solution was incubated at 37° C. for 6 hours.

After subsequent 21-fold dilution with a 20 mM potassium phosphate buffer (pH 7.5) containing 0.4M $(NH_4)_2SO_4$, the solution was allowed to stand on ice overnight. This refolding procedure yielded about 80 μg/ml of each of the mutant V8 protease D derivatives, i.e. the mutant V8 protease D derivatives V8D1, V8D5 and V8D8 derived from pV8D1, pV8D5 and pV8D8.

For purification of each of the proteases, $(NH_4)_2SO_4$ was added to a final concentration of 1.8M, and then 300 ml of the mixture was purified using a butyl Toyopearl 650M (product of Toso, KK.). The sample was added to a Φ16 mm×62 mm column equilibrized with a 10 mM potassium phosphate buffer (pH 7.5) containing 1.8M $(NH_4)_2SO_4$, and purification was conducted with a linear concentration gradient from 1.8M to 0M concentration of $(NH_4)_2SO_4$. Each of the proteases eluted near the 0.9M $(NH_4)_2SO_4$ concentration, and about 20 mg of each purified enzyme was obtained.

The activities of the purified enzymes were measured by the method described in Example 3.

Figure 17:
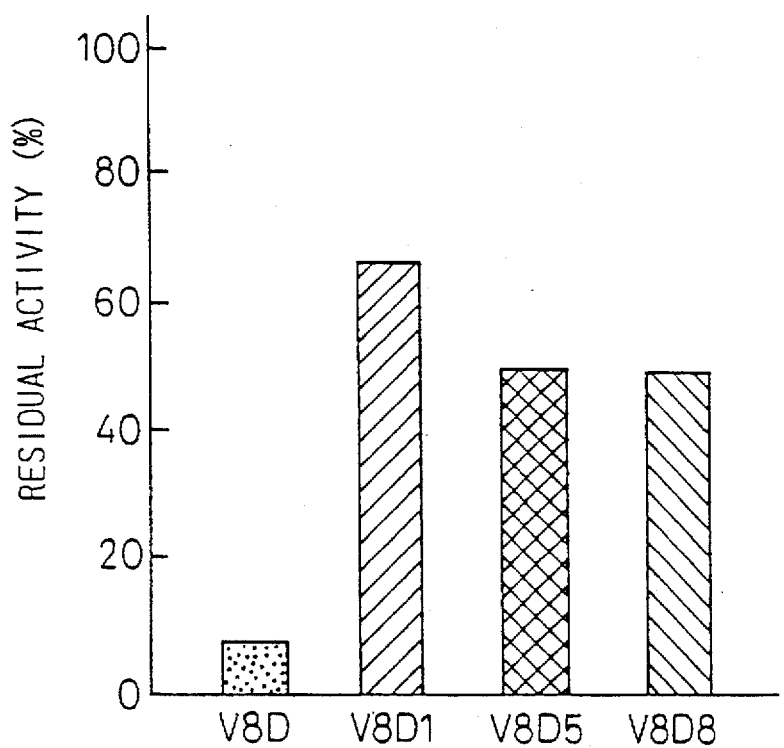
FIG. 17 shows the residual activities of the mutant V8 protease D derivatives (V8D1, V8D5 and V8D8) derived from plasmids pV8D1, pV8D5 and pV8D8, and the wild V8 protease D derivative (V8D) derived from pV8D, in the presence of 3M urea.

The purified V8D1, V8D5 and V8D8 were used to reexamine the resistance against urea. Each of the mutant enzymes (V8D1, V8D5 and V8D8) was added at 40 μl (concentration: 150 μg/ml) to 960 μl of a reaction mixture containing 3M urea, 50 mM Tris-HCl (pH 8.0) and 2% DMSO, and the mixtures were allowed to stand at 30° C. for 30 minutes, after which a synthetic substrate (Z-Phe-Leu- Glu-4-nitroanilide) was added to a final concentration of 0.4 mM, and the residual activity of each enzyme was measured with the activity immediately after addition of the enzyme defined as 100%. The wild V8 protease D derivative (V8D) produced from pV8D by the same procedure was used as a control. As a result, V8D1, V8D5 and V8D8 had higher residual activities than V8D, demonstrating that the introduction of their mutations produce mutant V8 protease D derivatives with improved resistance to urea (FIG. 17).

(2) Mutant V8 protease F derivatives

Mutations introduced into pV8F were also studied. Following the procedure outlined in FIG. 18, 0.7 kbp BglII-EcoRI fragments derived from pV8RPT(–)1, pV8RPT(–)5, pV8RPT(–)7, pV8RPT(–)8 and pV8RPT(–)158 were inserted into the 3.9 kbp BglII-EcoRI fragment of pV8F to construct pV8F1, pV8F5, pV8F7, pV8F8 and pV8F158.

JM01 strains possessing these plasmids were used to separate mutant V8 protease F derivatives having each of the mutations, i.e. the mutant V8 protease F derivatives V8F1, V8F5, V8F7, F8F8 and V8F158 derived from pV8F1, pV8F5, pV8F7, pV8F8 and pV8F158, by the method described above.

Figure 19:
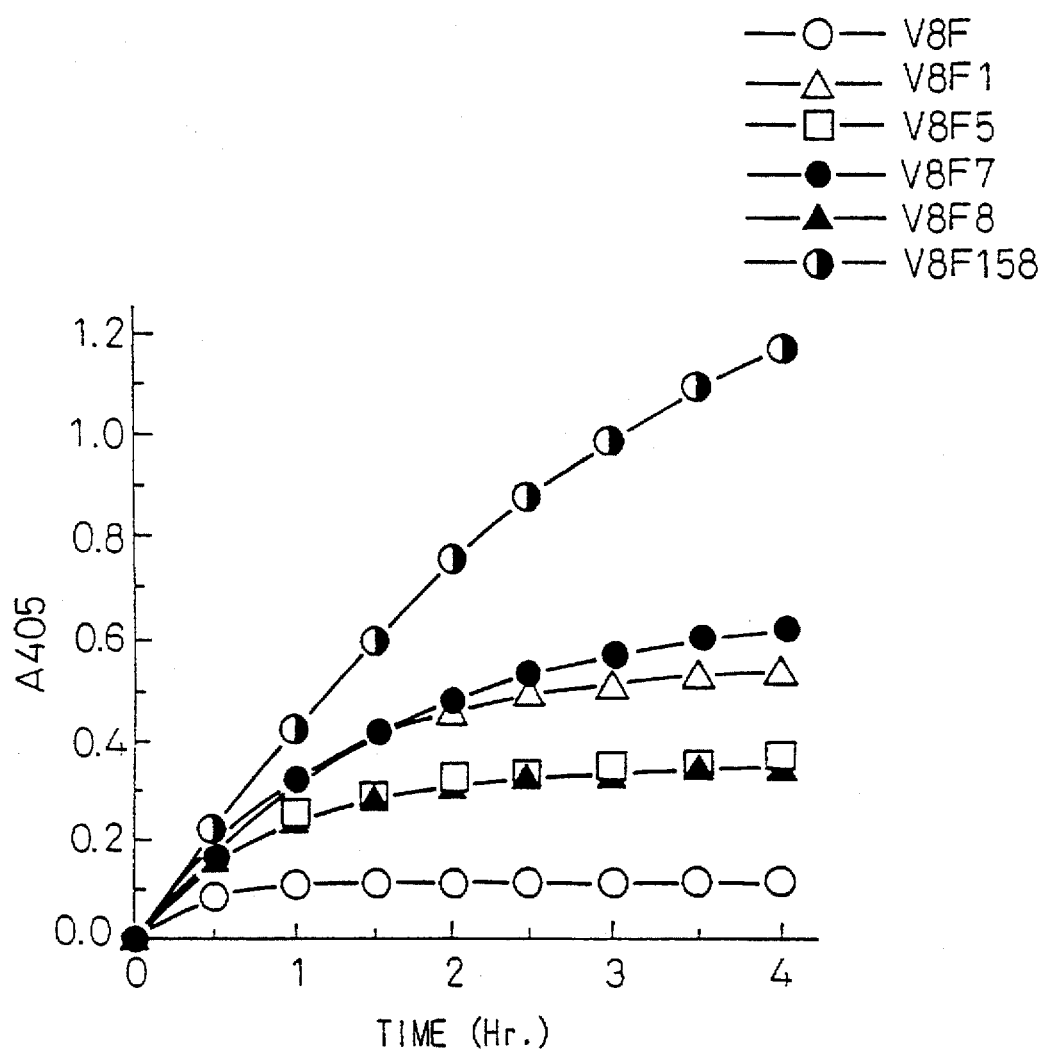
FIG. 19 shows the changes with time elapse in the reactivity of the mutant V8 protease F derivatives (V8F1, V8F5, V8F7, V8F and V8F158) derived from plasmids pV8F1, pV8F5, pV8F7, pV8F8 and pV8F158 and of the wild V8 protease F derivative (V8F) derived from pV8F, in the presence of 5M urea.

The purified V8F1, V8F5, V8F7, V8F8, F8F158 and the wild V8 protease F derivative (V8F) derived from pV8F as a control, which were produced by the same procedure, were used to reexamine the resistance against urea. As a result, each of the mutant enzymes was reconfirmed to have excellent urea resistance in the presence of 5M urea (FIG. 19), thus demonstrating the ability to produce mutant V8 protease F derivatives with excellent resistance to urea.

Example 10

Study of stability of V8F1, V8F5 and V8F8 against sodium dodecyl sulfate (0.1%) and heat (50° C.)

V8F1, V8F5 and V8F8 obtained in Example 9 were used to study their stability against sodium dodecyl sulfate (hereunder, SDS) and heat. For SDS stability, a solution containing 0.1% SDS, 50 mM Tris-HCl (pH 8.0) and an amount of each enzyme (V8F1, V8F5, V8F8) corresponding to 4.0 µg/ml enzyme activity of natural V8 protease was incubated at 30° C., and 900 µl thereof was taken at prescribed intervals, after which 100 µl of a solution containing 4 mM Z-Phe-Leu-Glu-4-nitroanilide and 20% DMSO was added and the residual activity was measured.

For the thermal stability at 50° C., a solution containing 50 mM Tris-HCl (pH 8.0) and an amount of each enzyme (V8F1, V8F5, V8F8) corresponding to 4.0 µg/ml enzyme activity of natural V8 protease was incubated at 50° C., and 900 µl thereof was taken at prescribed intervals, cooled on ice, and measured for residual activity.

Figure 20:
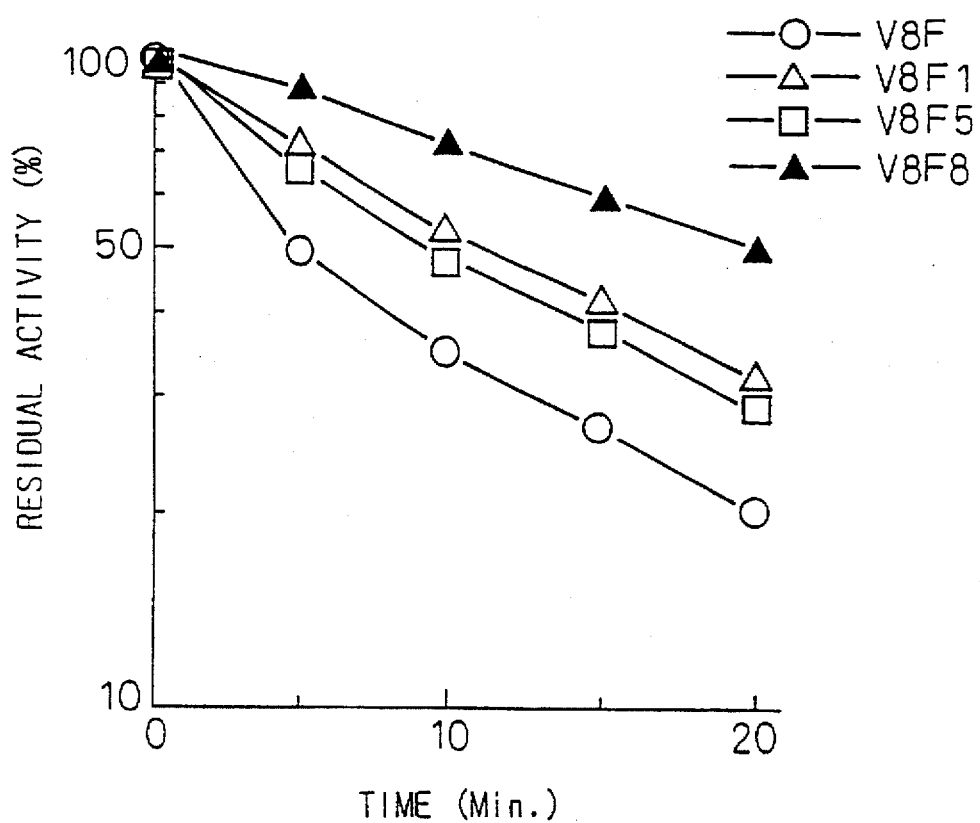
FIG. 20 shows the stabilities against 0.1% SDS of the mutant V8 protease F derivatives (V8F1, V8F5 and V8F8) derived from plasmids pV8F1, pV8F5 and pV8F8, and of the wild V8 protease F derivative (V8F).
Figure 21:
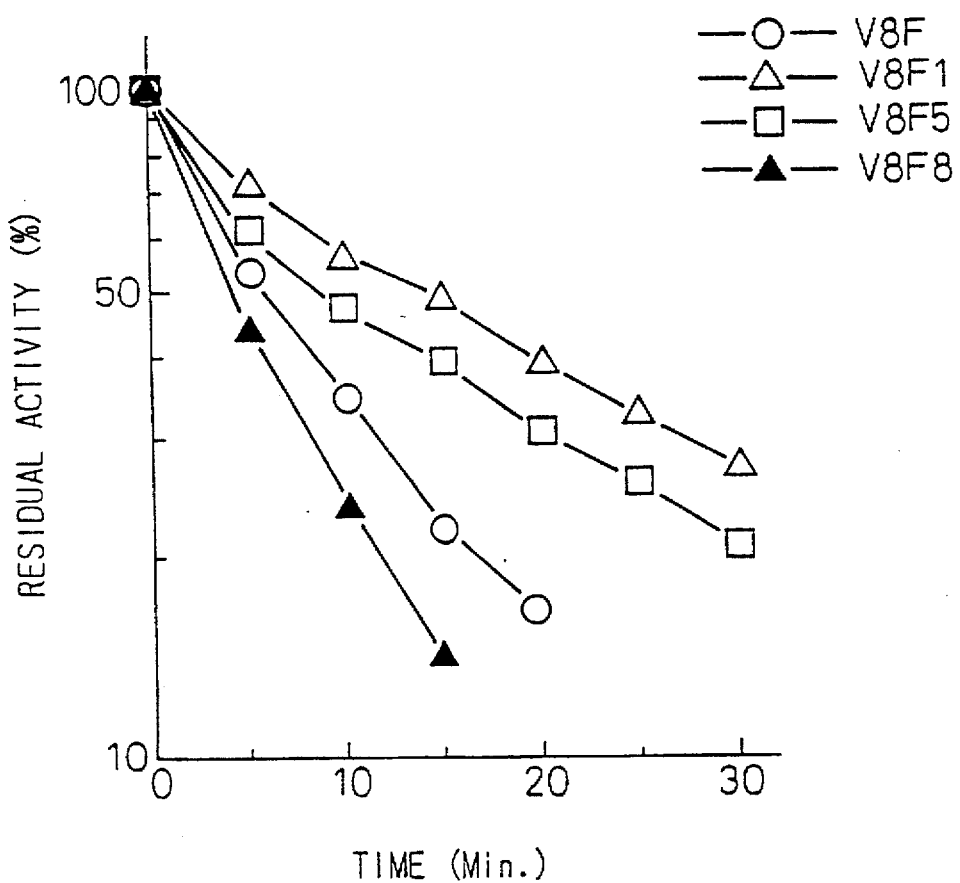
FIG. 21 shows the thermal stabilities at 50° C. of the mutant V8 protease F derivatives (V8F1, V8F5 and V8F8) derived from plasmids pV8F1, pV8F5 and pV8F8 and of the wild V8 protease F derivative (V8F).

As shown in FIG. 20, the mutant enzymes V8F1, V8F5 and V8F8 had lower inactivation rates than the wild form used as the control, and increased stability against 0.1% SDS. This demonstrated that the introduction of the 3 urea-resistant mutations Lys147Arg (V8F1), Asn71Ser (V8F5) and Asp44Glu (V8F8) is also effective against denaturation by SDS. Also, upon thermal inactivation at 50° C., V8Fl and V8F5 had lower inactivation rates than the wild V8F, showing that the mutations Lys147Arg and Asn71Ser impart thermal resistance (FIG. 21).

Example 11

Cleavage of fused protein by V8F158

V8F158 (the triple mutant V8 protease F derivative) was used for a protein cleavage experiment in the presence of urea. A fused protein derived from pG97S4DhCNP-22R5-3 was used as the substrate for the experiment. The fused protein β-gal97S4DhCNP-22R5-3 has a structure wherein a protective peptide (β-gal97S4D) and human C-type atrial natriuretic peptide (hCNP) are fused via a linker, and hCNP is released by the V8 protease (Japanese Unexamined Patent Publication No. 5-328992).

The natural V8 protease and V8F158 were compared in their ability to cleave hCNP from the fused peptide in the presence of 5M urea. The type of fused peptide derived from pG97S4DhCNP-22R5-3, the expression of the fused peptide, the recovery of the expressed inclusion body, the reaction conditions for V8 protease and the analysis of the fused protein and released hCNP were all according to the conditions described in Japanese Unexamined Patent Publication No. 5-328992. However, the urea concentration was adjusted to 5M for the reaction, and V8F158 was added in an amount corresponding to 4 µg/ml activity in terms of natural V8 protease.

After 30 minutes of reaction, the cleavage efficiency (proportion of fused protein cleaved) was calculated from the peak of HPLC, resulting in 60% for the natural V8 protease compared to 98% for V8F158, and thus the effectiveness of V8F158 in the presence of a high urea concentration was also demonstrated in the fused protein cleavage reaction.

Publicly known natural V8 protease is commonly used for the production of useful peptides, etc. by gene recombination methods because it still carries out some degree of cleavage reaction even in enzyme reaction solutions containing about 2M urea; however, as mentioned above, the enzymes of the present invention add even greater urea resistance to the properties of the natural enzyme. Thus, an enzyme according to the invention may be used to minimize inactivation of enzyme activity even in the presence of high concentrations of urea, to thus require lower amounts of enzyme to be added to urea-containing reaction systems and shorten reaction times. An additional advantage is that the ability to cleave proteins in the presence of high urea concentrations makes it possible to obtain hitherto unobtainable peptide fragments.

---

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 31 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

ACCGCTCGAG GTTATATTAC CAAATAACGA T     31

(2) INFORMATION FOR SEQ ID NO:2:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

TCGCGTCGAC TTATTGGTCA TCGTTGGCAA A     31

(2) INFORMATION FOR SEQ ID NO:3:

(i) SEQUENCE CHARACTERISTICS:
(A) LENGTH: 344 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:3:

```
Met  Thr  Met  Ile  Thr  Asp  Ser  Leu  Ala  Val  Val  Leu  Gln  Arg  Arg  Asp
1              5                        10                       15

Trp  Glu  Asn  Pro  Gly  Val  Thr  Gln  Leu  Asn  Arg  Leu  Ala  Ala  His  Pro
               20                       25                       30

Pro  Phe  Ala  Ser  Trp  Arg  Asn  Ser  Asp  Asp  Ala  Arg  Thr  Asp  Arg  Pro
          35                        40                       45

Ser  Gln  Gln  Leu  Arg  Ser  Leu  Asn  Gly  Glu  Trp  Arg  Phe  Ala  Trp  Phe
     50                        55                       60

Pro  Ala  Pro  Glu  Ala  Val  Pro  Asp  Ser  Leu  Leu  Asp  Ser  Asp  Leu  Pro
65                       70                       75                       80

Glu  Ala  Asp  Thr  Val  Val  Val  Pro  Ser  Asn  Trp  Gln  Met  His  Gly  Tyr
                    85                       90                       95

Asp  Ala  Glu  Leu  Arg  Leu  Tyr  Arg  Arg  His  His  Arg  Trp  Gly  Arg  Ser
               100                       105                      110

Gly  Ser  Pro  Leu  Arg  Ala  His  Glu  Gln  Phe  Leu  Glu  Val  Ile  Leu  Pro
          115                       120                      125

Asn  Asn  Asp  Arg  His  Gln  Ile  Thr  Asp  Thr  Thr  Asn  Gly  His  Tyr  Ala
     130                       135                      140

Pro  Val  Thr  Tyr  Ile  Gln  Val  Glu  Ala  Pro  Thr  Gly  Thr  Phe  Ile  Ala
145                       150                      155                      160

Ser  Gly  Val  Val  Val  Gly  Lys  Asp  Thr  Leu  Leu  Thr  Asn  Lys  His  Val
                    165                      170                      175

Val  Asp  Ala  Thr  His  Gly  Asp  Pro  His  Ala  Leu  Lys  Ala  Phe  Pro  Ser
               180                       185                      190

Ala  Ile  Asn  Gln  Asp  Asn  Tyr  Pro  Asn  Gly  Gly  Phe  Thr  Ala  Glu  Asn
          195                       200                      205

Ile  Thr  Lys  Tyr  Ser  Gly  Glu  Gly  Asp  Leu  Ala  Ile  Val  Lys  Phe  Ser
     210                       215                      220
```

| Pro | Asn | Glu | Gln | Asn | Lys | His | Ile | Gly | Glu | Val | Val | Lys | Pro | Ala | Thr |
| 225 | | | | | 230 | | | | 235 | | | | | | 240 |

| Met | Ser | Asn | Asn | Ala | Glu | Thr | Gln | Val | Asn | Gln | Asn | Ile | Thr | Val | Thr |
| | | | | 245 | | | | | 250 | | | | | 255 | |

| Gly | Tyr | Pro | Gly | Asp | Lys | Pro | Val | Ala | Thr | Met | Trp | Glu | Ser | Lys | Gly |
| | | | 260 | | | | | 265 | | | | | 270 | | |

| Lys | Ile | Thr | Tyr | Leu | Lys | Gly | Glu | Ala | Met | Gln | Tyr | Asp | Leu | Ser | Thr |
| | | 275 | | | | | 280 | | | | | 285 | | | |

| Thr | Gly | Gly | Asn | Ser | Gly | Ser | Pro | Val | Phe | Asn | Glu | Lys | Asn | Glu | Val |
| | 290 | | | | | 295 | | | | | 300 | | | | |

| Ile | Gly | Ile | His | Trp | Gly | Gly | Val | Pro | Asn | Glu | Phe | Asn | Gly | Ala | Val |
| 305 | | | | | 310 | | | | | 315 | | | | | 320 |

| Phe | Ile | Asn | Glu | Asn | Val | Arg | Asn | Phe | Leu | Lys | Gln | Asn | Ile | Glu | Asp |
| | | | | 325 | | | | | 330 | | | | | 335 | |

| Ile | His | Phe | Ala | Asn | Asp | Asp | Gln |
| | | | 340 | | | | |

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCGAGGCCT ATGACCATGA TTACGGAT                                                28

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TCGCGTCGAC TTATTGGTCA TCGTTGGCAA A                                       31

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ACCGCTCGAG GTTATATTAC CAAATAACGA T                                       31

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CAGGCGAAGG AGCGCTAGCA ATAGTTAAA                                29

( 2 ) INFORMATION FOR SEQ ID NO:8:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

TTTAACTATT GCTAGCGCTC CTTCGCCTG                                29

( 2 ) INFORMATION FOR SEQ ID NO:9:

( i ) SEQUENCE CHARACTERISTICS:
    ( A ) LENGTH: 532 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:9:

```
Met Thr Met Ile Thr Asp Ser Leu Ala Val Val Leu Gln Arg Arg Asp
 1           5                  10                  15
Trp Glu Asn Pro Gly Val Thr Gln Leu Asn Arg Leu Ala Ala His Pro
             20                  25                  30
Pro Phe Ala Ser Trp Arg Asn Ser Asp Asp Ala Arg Thr Asp Arg Pro
         35                  40                  45
Ser Gln Gln Leu Arg Ser Leu Asn Gly Glu Trp Arg Phe Ala Trp Phe
     50                  55                  60
Pro Ala Pro Glu Ala Val Pro Asp Ser Leu Leu Asp Ser Asp Leu Pro
 65                  70                  75                  80
Glu Ala Asp Thr Val Val Val Pro Ser Asn Trp Gln Met His Gly Tyr
                 85                  90                  95
Asp Ala Glu Leu Arg Leu Tyr Arg Arg His His Arg Trp Gly Arg Ser
             100                 105                 110
Gly Ser Pro Leu Arg Ala His Glu Gln Phe Leu Glu Val Ile Leu Pro
         115                 120                 125
Asn Asn Asp Arg His Gln Ile Thr Asp Thr Thr Asn Gly His Tyr Ala
     130                 135                 140
Pro Val Thr Tyr Ile Gln Val Glu Ala Pro Thr Gly Thr Phe Ile Ala
145                 150                 155                 160
Ser Gly Val Val Val Gly Lys Asp Thr Leu Leu Thr Asn Lys His Val
                 165                 170                 175
Val Asp Ala Thr His Gly Asp Pro His Ala Leu Lys Ala Phe Pro Ser
             180                 185                 190
Ala Ile Asn Gln Asp Asn Tyr Pro Asn Gly Gly Phe Thr Ala Glu Asn
         195                 200                 205
Ile Thr Lys Tyr Ser Gly Glu Gly Asp Leu Ala Ile Val Lys Phe Ser
     210                 215                 220
Pro Asn Glu Gln Asn Lys His Ile Gly Glu Val Val Lys Pro Ala Thr
225                 230                 235                 240
Met Ser Asn Asn Ala Glu Thr Gln Val Asn Gln Asn Ile Thr Val Thr
                 245                 250                 255
```

```
Gly Tyr Pro Gly Asp Lys Pro Val Ala Thr Met Trp Glu Ser Lys Gly
            260             265                 270

Lys Ile Thr Tyr Leu Lys Gly Glu Ala Met Gln Tyr Asp Leu Ser Thr
        275             280                 285

Thr Gly Gly Asn Ser Gly Ser Pro Val Phe Asn Glu Lys Asn Glu Val
    290             295             300

Ile Gly Ile His Trp Gly Gly Val Pro Asn Glu Phe Asn Gly Ala Val
305                 310             315                     320

Phe Ile Asn Glu Asn Val Arg Asn Phe Leu Lys Gln Asn Ile Glu Asp
                325                 330                 335

Arg Leu Tyr Arg Arg His His Arg Trp Gly Arg Ser Gly Ser Pro Leu
            340                 345             350

Arg Ala His Glu Gln Phe Leu Glu Cys Gly Asn Gly Lys Thr Ala Phe
        355                 360             365

Gln Val Leu Glu Glu Tyr Pro Asp Ser Gly Glu Asn Ile Val Asp Ala
    370                 375             380

Leu Ala Val Phe Leu Arg Arg Leu His Ser Ile Pro Val Cys Asn Cys
385                 390             395                     400

Pro Phe Asn Ser Asp Arg Val Phe Arg Leu Ala Gln Ala Gln Ser Arg
                405                 410                 415

Met Asn Asn Gly Leu Val Asp Ala Ser Asp Phe Asp Asp Glu Arg Asn
            420                 425                 430

Gly Trp Pro Val Glu Gln Val Trp Lys Glu Met His Lys Leu Leu Pro
        435                 440                 445

Phe Ser Pro Asp Ser Val Val Thr His Gly Asp Phe Ser Leu Asp Asn
    450                 455                 460

Leu Ile Phe Asp Glu Gly Lys Leu Ile Gly Cys Ile Asp Val Gly Arg
465                 470                 475                 480

Val Gly Ile Ala Asp Arg Tyr Gln Asp Leu Ala Ile Leu Trp Asn Cys
                485                 490                 495

Leu Gly Glu Phe Ser Pro Ser Leu Gln Lys Arg Leu Phe Gln Lys Tyr
            500                 505                 510

Gly Ile Asp Asn Pro Asp Met Asn Lys Leu Gln Phe His Leu Met Leu
        515                 520                 525

Asp Glu Phe Phe
        530
```

( 2 ) INFORMATION FOR SEQ ID NO:10:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Arg Leu Tyr Arg Arg His His Arg Trp Gly Arg Ser Gly Ser Pro Leu
1               5                   10                  15

Arg Ala His Glu Gln Phe Leu Glu
                20
```

( 2 ) INFORMATION FOR SEQ ID NO:11:

( i ) SEQUENCE CHARACTERISTICS:
        ( A ) LENGTH: 31 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:11:

ACCGCTCGAG GTTATATTAC CAAATAACGA T 31

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GACTTATTGG TCATCGAGCT CAAAATGGAT ATC 33

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AATATTGAAG AGCTCCGCCT ATATCGCCGA CAT 33

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GAATGGCAAA AGCTTATGCA TTTCTTT 27

( 2 ) INFORMATION FOR SEQ ID NO:15:

( i ) SEQUENCE CHARACTERISTICS:
        ( A ) LENGTH: 537 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met Thr Met Ile Thr Asp Ser Leu Ala Val Val Leu Gln Arg Arg Asp
 1               5                  10                  15
Trp Glu Asn Pro Gly Val Thr Gln Leu Asn Arg Leu Ala Ala His Pro
                20                  25                  30
Pro Phe Ala Ser Trp Arg Asn Ser Asp Asp Ala Arg Thr Asp Arg Pro
            35                  40                  45
Ser Gln Gln Leu Arg Ser Leu Asn Gly Glu Trp Arg Phe Ala Trp Phe
        50                  55                  60
Pro Ala Pro Glu Ala Val Pro Asp Ser Leu Leu Asp Ser Asp Leu Pro
65                  70                  75                  80
```

```
Glu Ala Asp Thr Val Val Pro Ser Asn Trp Gln Met His Gly Tyr
                85              90                  95
Asp Ala Glu Leu Arg Leu Tyr Arg Arg His His Arg Trp Gly Arg Ser
            100             105             110
Gly Ser Pro Leu Arg Ala His Glu Gln Phe Leu Glu Val Ile Leu Pro
        115             120             125
Asn Asn Asp Arg His Gln Ile Thr Asp Thr Thr Asn Gly His Tyr Ala
    130             135                 140
Pro Val Thr Tyr Ile Gln Val Glu Ala Pro Thr Gly Thr Phe Ile Ala
145             150             155                     160
Ser Gly Val Val Val Gly Lys Asp Thr Leu Leu Thr Asn Lys His Val
                165             170                 175
Val Asp Ala Thr His Gly Asp Pro His Ala Leu Lys Ala Phe Pro Ser
        180             185                 190
Ala Ile Asn Gln Asp Asn Tyr Pro Asn Gly Gly Phe Thr Ala Glu Asn
        195                 200             205
Ile Thr Lys Tyr Ser Gly Glu Gly Asp Leu Ala Ile Val Lys Phe Ser
    210             215             220
Pro Asn Glu Gln Asn Lys His Ile Gly Glu Val Val Lys Pro Ala Thr
225             230             235                     240
Met Ser Asn Asn Ala Glu Thr Gln Val Asn Gln Asn Ile Thr Val Thr
                245             250             255
Gly Tyr Pro Gly Asp Lys Pro Val Ala Thr Met Trp Glu Ser Lys Gly
            260             265             270
Lys Ile Thr Tyr Leu Lys Gly Glu Ala Met Gln Tyr Asp Leu Ser Thr
        275             280             285
Thr Gly Gly Asn Ser Gly Ser Pro Val Phe Asn Glu Lys Asn Glu Val
    290             295             300
Ile Gly Ile His Trp Gly Gly Val Pro Asn Glu Phe Asn Gly Ala Val
305             310             315                     320
Phe Ile Asn Glu Asn Val Arg Asn Phe Leu Lys Gln Asn Ile Glu Asp
                325             330             335
Ile His Phe Glu Leu Arg Leu Tyr Arg Arg His His Arg Trp Gly Arg
            340             345             350
Ser Gly Ser Pro Leu Arg Ala His Glu Gln Phe Leu Glu Cys Gly Asn
        355             360             365
Gly Lys Thr Ala Phe Gln Val Leu Glu Glu Tyr Pro Asp Ser Gly Glu
    370             375             380
Asn Ile Val Asp Ala Leu Ala Val Phe Leu Arg Arg Leu His Ser Ile
385             390             395                     400
Pro Val Cys Asn Cys Pro Phe Asn Ser Asp Arg Val Phe Arg Leu Ala
                405             410             415
Gln Ala Gln Ser Arg Met Asn Asn Gly Leu Val Asp Ala Ser Asp Phe
            420             425             430
Asp Asp Glu Arg Asn Gly Trp Pro Val Glu Gln Val Trp Lys Glu Met
        435             440             445
His Lys Leu Leu Pro Phe Ser Pro Asp Ser Val Val Thr His Gly Asp
    450             455             460
Phe Ser Leu Asp Asn Leu Ile Phe Asp Glu Gly Lys Leu Ile Gly Cys
465             470             475                     480
Ile Asp Val Gly Arg Val Gly Ile Ala Asp Arg Tyr Gln Asp Leu Ala
                485             490             495
```

-continued

| Ile | Leu | Trp | Asn<br>500 | Cys | Leu | Gly | Glu | Phe<br>505 | Ser | Pro | Ser | Leu | Gln<br>510 | Lys | Arg |
| Leu | Phe | Gln<br>515 | Lys | Tyr | Gly | Ile | Asp<br>520 | Asn | Pro | Asp | Met | Asn<br>525 | Lys | Leu | Gln |
| Phe | His<br>530 | Leu | Met | Leu | Asp | Glu<br>535 | Phe | Phe | | | | | | | |

We claim:

1. A mutant *Staphlococcus aureus* V8 protease comprising an amino acid sequence from the Valine at amino acid position 125 to the Aspartic acid at amino acid position 336 in SEQ ID NO: 3, wherein the Aspartic acid at amino acid position 168 is replaced with Glutamic acid, the Asparagine at amino acid position 195 is replaced with Serine, and/or the Lysine at amino acid position 271 is replaced with Arginine.

2. A mutant *Staphylococcus aureus* V8 protease comprising the amino acid sequence from the Arginine at amino acid position 105 to the Glutamine at amino acid position 344 of SEQ ID NO: 3, wherein the Aspartic acid at amino acid position 168 is replaced with Glutamic acid, the Asparagine at amino acid position 195 is replaced with Serine, and/or the Lysine at amino acid position 271 is replaced with Arginine.

3. A mutant *Staphylococcus aureus* V8 protease comprising the amino acid sequence from the Arginine at amino acid position 105 to the Arginine at amino acid position 340 of SEQ ID NO: 9, wherein the Aspartic acid at amino acid position 168 is replaced with Glutamic acid, the Asparagine at amino acid position 195 is replaced with Serine, and/or the Lysine at amino acid position 271 is replaced with Arginine.

4. A mutant *Staphylococcus aureus* V8 protease comprising as the amino acid sequence from the Arginine at amino acid position 105 to the Arginine at amino acid position 345 of SEQ ID NO: 15, wherein the Aspartic acid at amino acid position 168 is replaced with Glutamic acid, the Asparagine at amino acid position 195 is replaced with Serine, and/or the Lysine at amino acid position 271 is replaced with Arginine.

5. A gene coding for a mutant *Staphylococcus aureus* V8 protease according to claim 1.

6. A gene coding for a mutant *Staphylococcus aureus* V8 protease according to claim 2.

7. A gene coding for a mutant *Staphylococcus aureus* V8 protease according to claim 3.

8. A gene coding for a mutant *Staphylococcus aureus* V8 protease according to claim 4.

9. An expression vector comprising a gene according to claim 5.

10. An expression vector comprising a gene according to claim 6.

11. An expression vector comprising a gene according to claim 7.

12. An expression vector comprising a gene according to claim 8.

13. Recombinant cells transformed with an expression vector according to claim 9.

14. Recombinant cells transformed with an expression vector according to claim 10.

15. Recombinant cells transformed with an expression vector according to claim 11.

16. Recombinant cells transformed with an expression vector according to claim 12.

17. A process for production of a mutant *Staphylococcus aureus* V8 protease according to claim 1, comprising the steps of culturing recombinant cells transformed with an expression vector comprising a gene coding for said mutant protease in a medium, and recovering the mutant protease from the culture.

18. A process for production of a mutant *Staphylococcus aureus* V8 protease according to claim 2, comprising the steps of culturing recombinant cells transformed with an expression vector comprising a gene coding for said mutant protease in a medium, and recovering the mutant protease from the culture.

19. A process for production of a mutant *Staphylococcus aureus* V8 protease according to claim 3, comprising the steps of culturing recombinant cells transformed with an expression vector comprising a gene coding for said mutant protease in a medium, and recovering the mutant protease from the culture.

20. A process for production of a mutant *Staphylococcus aureus* V8 protease according to claim 4, comprising the steps of culturing recombinant cells transformed with an expression vector comprising a gene coding for said mutant protease in a medium, and recovering the mutant protease from the culture.

21. A process for production of a mutant *Staphylococcus aureus* V8 protease comprising an amino acid sequence from the Valine at amino acid position 125 to the Aspartic acid at amino acid position 366 in SEQ ID NO: 3, wherein the Aspartic acid at amino acid position 168, the Asparagine at amino acid position 195 and/or the Lysine at amino acid position 271 is replaced with another amino acid, comprising the steps of culturing recombinant cells transformed with an expression vector comprising a gene coding for said mutant protease in a medium and recovering the mutant protease.

22. A process for production of a mutant *Staphylococcus aureus* V8 protease comprising an amino acid sequence from the Arginine at amino acid position 105 to the Glutamine at amino acid position 344 in SEQ ID NO:3, wherein the Aspartic acid at amino acid position 168 , the Asparagine at amino acid position 195 and/or the Lysine at amino acid position 271 is replaced with another amino acid, comprising the steps of culturing recombinant cells transformed with an expression vector comprising a gene coding for said mutant protease in a medium and recovering the mutant protease.

23. A process for production of a mutant *Staphylococcus aureus* V8 protease comprising an amino acid sequence from the Arginine at amino acid position 105 to the Arginine at amino acid position 340 in SEQ ID NO: 9, wherein the Aspartic acid at amino acid position 168, the Asparagine at amino acid position 195 and/or the Lysine at amino acid position 271 is replaced with another amino acid, comprising the steps of culturing recombinant cells transformed with an expression vector comprising a gene coding for said mutant protease in a medium and recovering the mutant protease.

24. A process for production of a mutant *Staphylococcus aureus* V8 protease comprising an amino acid sequence from the Arginine at amino acid position 105 to the Arginine at amino acid position 345 in SEQ ID NO: 15, wherein the Aspartic acid at amino acid position 168, the Asparagine at amino acid position 195 and/or the Lysine at amino acid position 271 is replaced with another amino acid, comprising the steps of culturing recombinant cells transformed with an expression vector comprising a gene coding for said mutant protease in a medium and recovering the mutant protease.

* * * * *